US008906601B2

(12) United States Patent
Dove et al.

(10) Patent No.: US 8,906,601 B2
(45) Date of Patent: Dec. 9, 2014

(54) METHODS FOR STABILIZING A BIOPROSTHETIC TISSUE BY CHEMICAL MODIFICATION OF ANTIGENIC CARBOHYDRATES

(75) Inventors: Jeffrey S. Dove, Santa Ana, CA (US); Tara J. Tod, Tustin, CA (US)

(73) Assignee: Edwardss Lifesciences Corporation, Irvine, CA (US)

(*) Notice: Subject to any disclaimer, the term of this patent is extended or adjusted under 35 U.S.C. 154(b) by 270 days.

(21) Appl. No.: 13/163,557

(22) Filed: Jun. 17, 2011

(65) Prior Publication Data

US 2011/0311493 A1    Dec. 22, 2011

Related U.S. Application Data

(60) Provisional application No. 61/355,943, filed on Jun. 17, 2010.

(51) Int. Cl.
| *A01N 1/00* | (2006.01) |
| *A61L 27/54* | (2006.01) |
| *A61L 27/50* | (2006.01) |
| *A61L 27/36* | (2006.01) |

(52) U.S. Cl.
CPC ............... *A61L 27/50* (2013.01); *A61L 27/54* (2013.01); *A61L 2430/20* (2013.01); *A61L 2430/40* (2013.01); *A61L 27/3687* (2013.01)
USPC ............................................. 435/1.1; 623/2.1

(58) Field of Classification Search
None
See application file for complete search history.

(56) References Cited

U.S. PATENT DOCUMENTS

| 2,393,580 | A | 1/1946 | Weiskopf |
| 2,484,813 | A | 10/1949 | Bower |
| 2,567,929 | A | 9/1951 | Fessenden |
| 3,002,895 | A | 10/1961 | Freedman |
| 3,093,439 | A | 6/1963 | Bothwell |
| 3,870,789 | A | 3/1975 | Mikat |
| 3,927,422 | A | 12/1975 | Sawyer |
| 3,961,097 | A | 6/1976 | Gravlee, Jr. |
| 3,966,401 | A | 6/1976 | Hancock et al. |
| 4,050,893 | A | 9/1977 | Hancock et al. |
| 4,067,091 | A | 1/1978 | Backman |
| 4,082,507 | A | 4/1978 | Sawyer |
| 4,120,649 | A | 10/1978 | Schechter |
| 4,120,991 | A | 10/1978 | Ornstein et al. |
| 4,197,658 | A | 4/1980 | Fraser |
| 4,207,689 | A | 6/1980 | Romera-Sierra et al. |
| 4,294,753 | A | 10/1981 | Urist |
| 4,320,157 | A | 3/1982 | von Hagens |
| 4,323,358 | A | 4/1982 | Lentz et al. |
| 4,328,256 | A | 5/1982 | Romero-Sierra et al. |
| 4,347,671 | A | 9/1982 | Dias et al. |
| 4,350,492 | A | 9/1982 | Wright et al. |
| 4,372,743 | A | 2/1983 | Lane |
| 4,378,224 | A | 3/1983 | Nimni et al. |
| 4,402,697 | A | 9/1983 | Pollock et al. |
| 4,405,327 | A | 9/1983 | Pollock |
| 4,481,009 | A | 11/1984 | Nashef |
| 4,553,974 | A | 11/1985 | Dewanjee |
| 4,599,084 | A | 7/1986 | Nashef |
| 4,624,822 | A | 11/1986 | Arru et al. |
| 4,647,283 | A | 3/1987 | Carpentier et al. |
| 4,648,881 | A | 3/1987 | Carpentier et al. |
| 4,655,773 | A | 4/1987 | Grassi |
| 4,676,070 | A | 6/1987 | Linner |
| 4,729,139 | A | 3/1988 | Nashef |
| 4,753,652 | A | 6/1988 | Langer et al. |
| 4,770,665 | A | 9/1988 | Nashef |
| 4,776,853 | A | 10/1988 | Klement et al. |
| 4,786,287 | A | 11/1988 | Nashef et al. |
| 4,800,603 | A | 1/1989 | Jaffe |
| 4,831,065 | A | 5/1989 | Pietsch et al. |
| 4,838,888 | A | 6/1989 | Nashef |
| 4,865,871 | A | 9/1989 | Livesey et al. |
| 4,885,005 | A | 12/1989 | Nashef et al. |
| 4,891,319 | A | 1/1990 | Roser |
| 4,911,713 | A | 3/1990 | Sauvage et al. |
| 4,958,008 | A | 9/1990 | Petite et al. |
| 4,969,912 | A | 11/1990 | Kelman et al. |
| 4,975,526 | A | 12/1990 | Kuberasampath et al. |
| 4,976,733 | A | 12/1990 | Girardot |
| 4,990,131 | A | 2/1991 | Dardik et al. |

(Continued)

FOREIGN PATENT DOCUMENTS

| WO | 84/01894 A1 | 5/1984 |
| WO | 95/11047 A1 | 4/1995 |

(Continued)

OTHER PUBLICATIONS

Mercuri et al., Biomaterials 28, 2007, pp. 496-503.*
Carpentier, A., et al., "Biological Factors Affecting Long-Term Results of Valvular Heterografts," Forty-ninth Meeting of the American Association for Thoracic Surgery, San Francisco, CA, Mar. 31-Apr. 2, 1969.
Chanda, J., et al., "Heparin in Calcification Prevention of Porcine Pericardial Bioprostheses," Biomaterials, Elsevier Science Publishers, vol. 18, No. 16, ISSN: 0142-9612, Aug. 1, 1997.
Dahm, Manfred, et al., "Effects of Surface Seeding with Vital Cells on the Calcium Uptake of Biological Materials for Heart Valve Replacement," J Heart Valve Dis, vol. 5, No. 2, Mar. 1996, 148-151.

(Continued)

*Primary Examiner* — Allison Fox
*Assistant Examiner* — Yvonne Pyla
(74) *Attorney, Agent, or Firm* — AnneMarie Kaiser; Pui Tong Ho

(57) ABSTRACT

Methods are provided herein for modifying antigenic carbohydrate epitopes within a xenographic bioprosthetic tissue by oxidation of vicinal diols to form aldehydes or acids and subsequence reductive amination of aldehydes to form stable secondary amines, or amidation or esterification of acids to form stable amides or esters. Advantageously, methods provided herein mitigate the antigenicity of the bioprosthetic tissue while leaving the overall tissue structure substantially undisturbed, and thereby enhance the durability, safety and performance of the bioprosthetic implant.

48 Claims, 10 Drawing Sheets

(56) References Cited

U.S. PATENT DOCUMENTS

| | | |
|---|---|---|
| 4,994,030 A | 2/1991 | Glowczewskie, Jr. et al. |
| 4,994,237 A | 2/1991 | Login et al. |
| 4,996,054 A | 2/1991 | Pietsch et al. |
| 5,002,566 A | 3/1991 | Carpentier et al. |
| 5,011,913 A | 4/1991 | Benedict et al. |
| 5,024,830 A | 6/1991 | Linner |
| 5,044,165 A | 9/1991 | Linner et al. |
| 5,051,401 A | 9/1991 | Sikes |
| 5,068,086 A | 11/1991 | Sklenak et al. |
| 5,068,100 A | 11/1991 | McClanahan |
| 5,080,670 A | 1/1992 | Imamura et al. |
| 5,094,661 A | 3/1992 | Levy et al. |
| 5,104,405 A | 4/1992 | Nimni |
| 5,108,923 A | 4/1992 | Benedict et al. |
| 5,116,564 A | 5/1992 | Jansen et al. |
| 5,131,908 A | 7/1992 | Dardik et al. |
| 5,147,514 A | 9/1992 | Mechanic |
| 5,149,621 A | 9/1992 | McNally et al. |
| 5,149,653 A | 9/1992 | Roser |
| 5,154,007 A | 10/1992 | Piunno et al. |
| 5,200,399 A | 4/1993 | Wettlaufer et al. |
| 5,215,541 A | 6/1993 | Nashef et al. |
| 5,275,954 A | 1/1994 | Wolfinbarger et al. |
| 5,279,612 A | 1/1994 | Eberhardt |
| 5,290,558 A | 3/1994 | O'Leary et al. |
| 5,296,583 A | 3/1994 | Levy |
| 5,332,475 A | 7/1994 | Mechanic |
| 5,336,616 A | 8/1994 | Livesey et al. |
| 5,368,608 A | 11/1994 | Levy et al. |
| 5,397,353 A | 3/1995 | Oliver et al. |
| 5,424,047 A | 6/1995 | Zwingenberger et al. |
| 5,436,291 A | 7/1995 | Levy et al. |
| 5,437,287 A | 8/1995 | Phillips et al. |
| 5,447,536 A | 9/1995 | Girardot et al. |
| 5,447,724 A | 9/1995 | Helmus et al. |
| 5,460,962 A | 10/1995 | Kemp |
| 5,476,516 A | 12/1995 | Seifter et al. |
| 5,507,813 A | 4/1996 | Dowd et al. |
| 5,509,932 A | 4/1996 | Keogh et al. |
| 5,556,379 A | 9/1996 | Wolfinbarger |
| 5,558,875 A | 9/1996 | Wang |
| 5,595,571 A | 1/1997 | Jaffe et al. |
| 5,613,982 A | 3/1997 | Goldstein |
| 5,632,778 A | 5/1997 | Goldstein |
| 5,645,587 A | 7/1997 | Chanda et al. |
| 5,674,298 A | 10/1997 | Levy et al. |
| 5,679,112 A | 10/1997 | Levy et al. |
| 5,695,820 A | 12/1997 | Davis et al. |
| 5,697,972 A | 12/1997 | Kim et al. |
| 5,720,777 A | 2/1998 | Jaffe et al. |
| 5,733,339 A | 3/1998 | Girardot et al. |
| 5,746,775 A | 5/1998 | Levy et al. |
| 5,762,600 A | 6/1998 | Bruchman et al. |
| 5,766,520 A | 6/1998 | Bronshtein |
| 5,769,780 A | 6/1998 | Hata et al. |
| 5,773,285 A | 6/1998 | Park |
| 5,776,182 A | 7/1998 | Bruchman et al. |
| 5,782,914 A | 7/1998 | Schankereli |
| 5,782,915 A | 7/1998 | Stone |
| 5,782,931 A | 7/1998 | Yang et al. |
| 5,792,603 A | 8/1998 | Dunkelman et al. |
| 5,843,180 A | 12/1998 | Jaffe et al. |
| 5,843,181 A | 12/1998 | Jaffe et al. |
| 5,843,182 A | 12/1998 | Goldstein |
| 5,855,620 A | 1/1999 | Bishopric et al. |
| 5,856,102 A | 1/1999 | Bierke-Nelson et al. |
| 5,856,172 A | 1/1999 | Greenwood et al. |
| 5,862,806 A | 1/1999 | Cheung |
| 5,865,849 A | 2/1999 | Stone |
| 5,873,812 A | 2/1999 | Ciana et al. |
| 5,879,383 A | 3/1999 | Bruchman et al. |
| 5,882,850 A | 3/1999 | Khor et al. |
| 5,882,918 A | 3/1999 | Goffe |
| 5,899,936 A | 5/1999 | Goldstein |
| 5,902,338 A | 5/1999 | Stone |
| 5,904,718 A | 5/1999 | Jefferies |
| 5,911,951 A | 6/1999 | Girardot et al. |
| 5,913,900 A | 6/1999 | Stone |
| 5,919,472 A | 7/1999 | Trescony et al. |
| 5,922,027 A | 7/1999 | Stone |
| 5,931,969 A | 8/1999 | Carpentier et al. |
| 5,935,168 A | 8/1999 | Yang et al. |
| 5,945,319 A | 8/1999 | Keogh |
| 5,977,153 A | 11/1999 | Camiener |
| 5,987,720 A | 11/1999 | Yamamoto |
| 5,993,844 A | 11/1999 | Abraham et al. |
| 6,008,292 A | 12/1999 | Lee et al. |
| 6,017,741 A | 1/2000 | Keogh |
| 6,024,735 A | 2/2000 | Wolfinbarger, Jr. |
| 6,063,120 A | 5/2000 | Stone |
| 6,066,160 A | 5/2000 | Colvin et al. |
| 6,093,204 A | 7/2000 | Stone |
| 6,093,530 A | 7/2000 | McIlroy et al. |
| 6,106,555 A | 8/2000 | Yang |
| 6,117,979 A | 9/2000 | Hendriks et al. |
| 6,121,041 A | 9/2000 | Mirsch, II et al. |
| 6,132,473 A | 10/2000 | Williams et al. |
| 6,132,986 A | 10/2000 | Pathak et al. |
| 6,156,531 A | 12/2000 | Pathak et al. |
| 6,166,184 A | 12/2000 | Hendriks et al. |
| 6,177,514 B1 | 1/2001 | Pathak et al. |
| 6,190,407 B1 | 2/2001 | Ogle et al. |
| 6,193,749 B1 | 2/2001 | Schroeder et al. |
| 6,203,755 B1 | 3/2001 | Odland |
| 6,206,917 B1 | 3/2001 | Williams et al. |
| 6,210,957 B1 | 4/2001 | Carpentier et al. |
| 6,214,054 B1 | 4/2001 | Cunanan et al. |
| 6,214,055 B1 | 4/2001 | Simionescu et al. |
| 6,231,608 B1 | 5/2001 | Stone |
| 6,231,614 B1 | 5/2001 | Yang |
| 6,251,579 B1 | 6/2001 | Moore et al. |
| 6,254,635 B1 | 7/2001 | Schroeder et al. |
| 6,258,320 B1 | 7/2001 | Persing et al. |
| 6,267,786 B1 | 7/2001 | Stone |
| 6,277,555 B1 | 8/2001 | Duran et al. |
| 6,287,338 B1 | 9/2001 | Sarnowski et al. |
| 6,290,991 B1 | 9/2001 | Roser et al. |
| 6,302,909 B1 | 10/2001 | Ogle et al. |
| 6,312,474 B1 | 11/2001 | Francis et al. |
| 6,322,593 B1 | 11/2001 | Pathak et al. |
| 6,322,994 B1 | 11/2001 | Reid |
| 6,328,762 B1 | 12/2001 | Anderson et al. |
| 6,352,708 B1 | 3/2002 | Duran et al. |
| 6,364,905 B1 | 4/2002 | Simpson et al. |
| 6,372,228 B1 | 4/2002 | Gregory |
| 6,375,680 B1 | 4/2002 | Carlyle |
| 6,376,244 B1 | 4/2002 | Atala |
| 6,383,732 B1 | 5/2002 | Stone |
| 6,391,538 B1 | 5/2002 | Vyavahare et al. |
| 6,394,096 B1 | 5/2002 | Constantz |
| 6,448,076 B2 | 9/2002 | Dennis et al. |
| 6,468,660 B2 | 10/2002 | Ogle et al. |
| 6,471,723 B1 | 10/2002 | Ashworth et al. |
| 6,479,079 B1 | 11/2002 | Pathak et al. |
| 6,506,339 B1 | 1/2003 | Girardot et al. |
| 6,509,145 B1 | 1/2003 | Torrianni |
| 6,527,979 B2 | 3/2003 | Constantz et al. |
| 6,531,310 B1 | 3/2003 | Mirsch, II et al. |
| 6,534,004 B2 | 3/2003 | Chen et al. |
| 6,547,827 B2 | 4/2003 | Carpentier et al. |
| 6,561,970 B1 | 5/2003 | Carpentier et al. |
| 6,569,200 B2 | 5/2003 | Wolfinbarger, Jr. et al. |
| 6,582,464 B2 | 6/2003 | Gabbay |
| 6,586,006 B2 | 7/2003 | Roser et al. |
| 6,586,573 B1 | 7/2003 | Besman et al. |
| 6,589,591 B1 | 7/2003 | Mansouri et al. |
| 6,605,667 B1 | 8/2003 | Badejo et al. |
| 6,613,278 B1 | 9/2003 | Mills et al. |
| 6,617,142 B2 | 9/2003 | Keogh et al. |
| 6,630,001 B2 | 10/2003 | Duran et al. |
| 6,652,594 B2 | 11/2003 | Francis et al. |
| 6,653,062 B1 | 11/2003 | DePablo et al. |
| 6,660,265 B1 | 12/2003 | Chen et al. |
| 6,685,940 B2 | 2/2004 | Andya et al. |

(56) References Cited

U.S. PATENT DOCUMENTS

| | | |
|---|---|---|
| 6,696,074 B2 | 2/2004 | Dai et al. |
| 6,734,018 B2 | 5/2004 | Wolfinbarger, Jr. et al. |
| 6,753,181 B2 | 6/2004 | Atala |
| 6,758,865 B1 | 7/2004 | Stone et al. |
| 6,790,229 B1 | 9/2004 | Berreklouw |
| 6,797,000 B2 | 9/2004 | Simpson et al. |
| 6,828,310 B2 | 12/2004 | Barresi et al. |
| 6,861,211 B2 | 3/2005 | Levy et al. |
| 6,878,168 B2 | 4/2005 | Carpentier et al. |
| 6,893,666 B2 | 5/2005 | Spievack |
| 6,908,591 B2 | 6/2005 | MacPhee et al. |
| 6,919,172 B2 | 7/2005 | DePablo et al. |
| 6,933,326 B1 | 8/2005 | Griffey et al. |
| 7,008,763 B2 | 3/2006 | Cheung |
| 7,063,726 B2 | 6/2006 | Crouch et al. |
| 7,078,163 B2 | 7/2006 | Torrianni |
| 7,087,723 B2 | 8/2006 | Besman et al. |
| 7,318,998 B2 | 1/2008 | Goldstein et al. |
| 7,338,757 B2 | 3/2008 | Wolfinbarger, Jr. et al. |
| 7,354,749 B2 | 4/2008 | Fisher et al. |
| 7,358,284 B2 | 4/2008 | Griffey et al. |
| 7,594,974 B2 | 9/2009 | Cali et al. |
| 7,645,568 B2 | 1/2010 | Stone |
| 7,648,676 B2 | 1/2010 | Mills et al. |
| 2001/0000804 A1 | 5/2001 | Goldstein et al. |
| 2001/0020191 A1 | 9/2001 | Williams et al. |
| 2001/0025196 A1 | 9/2001 | Chinn et al. |
| 2001/0032024 A1 | 10/2001 | Cunanan et al. |
| 2001/0039459 A1 | 11/2001 | Stone |
| 2002/0001834 A1 | 1/2002 | Keogh et al. |
| 2002/0111532 A1 | 8/2002 | Pathak et al. |
| 2003/0035843 A1 | 2/2003 | Livesey et al. |
| 2003/0118981 A1* | 6/2003 | Torrianni .................. 435/1.1 |
| 2003/0125805 A1 | 7/2003 | Johnson et al. |
| 2003/0135284 A1 | 7/2003 | Crouch et al. |
| 2003/0167089 A1 | 9/2003 | Lane |
| 2004/0030381 A1 | 2/2004 | Shu |
| 2004/0086543 A1 | 5/2004 | Keogh et al. |
| 2004/0157206 A1* | 8/2004 | Fisher et al. .................. 435/1.1 |
| 2004/0158320 A1 | 8/2004 | Simionescu et al. |
| 2004/0193259 A1 | 9/2004 | Gabbay |
| 2005/0079200 A1 | 4/2005 | Rathenow et al. |
| 2005/0119736 A1 | 6/2005 | Zilla et al. |
| 2005/0136510 A1 | 6/2005 | Hendriks et al. |
| 2006/0099326 A1 | 5/2006 | Keogh et al. |
| 2006/0110370 A1 | 5/2006 | Pathak et al. |
| 2006/0159641 A1 | 7/2006 | Girardot et al. |
| 2006/0177426 A1 | 8/2006 | Gibson et al. |
| 2006/0210960 A1 | 9/2006 | Livesey et al. |
| 2006/0217804 A1 | 9/2006 | Dove |
| 2006/0217805 A1 | 9/2006 | Dove |
| 2007/0020248 A1* | 1/2007 | Everaerts et al. .......... 424/93.21 |
| 2007/0050014 A1 | 3/2007 | Johnson |
| 2007/0292459 A1 | 12/2007 | Cooper et al. |
| 2008/0302372 A1 | 12/2008 | Davidson et al. |
| 2008/0319166 A1 | 12/2008 | Shen |
| 2009/0041729 A1 | 2/2009 | Wolfinbarger, Jr. et al. |
| 2009/0164005 A1 | 6/2009 | Dove et al. |

FOREIGN PATENT DOCUMENTS

| | | |
|---|---|---|
| WO | 95/22361 A1 | 8/1995 |
| WO | 95/34332 A1 | 12/1995 |
| WO | 96/04028 A1 | 2/1996 |
| WO | 96/13227 A1 | 5/1996 |
| WO | 00/32252 A1 | 6/2000 |
| WO | 03/037227 A2 | 5/2003 |
| WO | 2004/082536 A1 | 9/2004 |
| WO | 2006/099334 A2 | 9/2006 |
| WO | 2006/112708 A1 | 10/2006 |

OTHER PUBLICATIONS

Jayakrishnan, A., et al., "Glutaraldehyde as a Fixative in Bioprostheses and Drug Delivery Matrices," Biomaterials,, vol. 17, Issue 5, 1996, pp. 471-484.

Khora, Eugene, "Methods for the Treatment of Collagenous Tissues for Bioprostheses," Biomaterials, vol. 18, Issue 2, Jan. 1997, pp. 95-105.

R Parker, et al. Storage of Heart Valve Allografts in Glycerol With Subsequent Antibiotic Sterilisation, Thorax, 1978, 638-645, vol. 33:5, British Thoracic Society, London, UK.

Zilla, P., et al., "Carbodiimide Treatment Dramatically Potentiates the Anticalcific Effect of Alpha-Amino Oleic Acid on Glutaraldehyde-Fixed Aortic Wall Tissue," The Annals of Thoracic Surgery, Elsevier, vol. 79, No. 3, ISSN: 0003-4975; Mar. 1, 2005.

International Search Report from corresponding International Application No. PCT/US2011/040984 dated Feb. 24, 2012.

* cited by examiner

Fresh Peri (No Treatment), exp. #2

Fresh/Autologen exp. #1

Lifenet Decell Peri, exp. #4

In-House Decell Peri, exp. #3

Another Commercial Decelled Peri, exp. #5

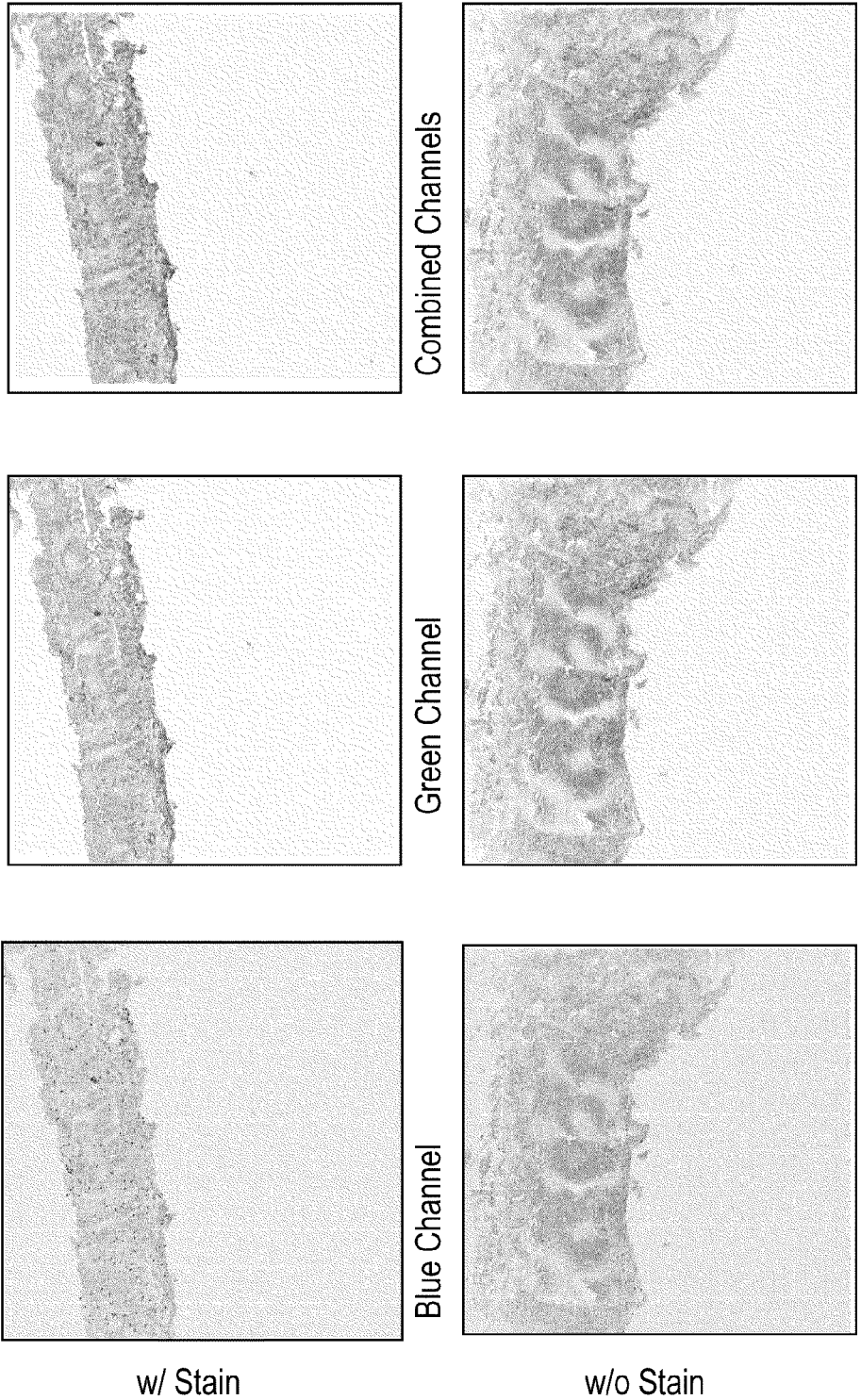

METHODS FOR STABILIZING A BIOPROSTHETIC TISSUE BY CHEMICAL MODIFICATION OF ANTIGENIC CARBOHYDRATES

RELATED APPLICATIONS

Related Application Data

The present application claims priority under 35 U.S.C. § 119(e) to U.S. Provisional Application No. 61/355,943 filed Jun. 17, 2010.

FIELD

Methods are provided herein relating to the field of bioprosthetic implants, and more particularly to the treatment of bioprosthetic tissues to decrease post-implantation antigenicity and calcification in host subjects.

BACKGROUND

A primary limitation of bioprosthetic implants made from animal tissues is the occurrence of hyperacute rejection reactions in transplant recipients. Such reactions are driven largely by the presence of antigenic carbohydrate epitopes within implanted tissues, the most common of which is the α-GAL glycoprotein epitope: D Galactose (α 1-3) Galactose (β1-4) N acetyl Glucosamine-R-motif (α-GAL) is found on vascular endothelial tissues of all species with the exception of old world monkeys, great apes, and humans. The presence of α-GAL on harvested animal donor tissues elicits an immediate and powerful immune response after transplantation into humans that can quickly destroy surrounding tissues and/or organs. The rapidity of the rejection response is due to very high levels of preformed anti-α-GAL antibodies in human subjects (nearly 1% of all antibodies in human blood are anti-α-GAL antibodies). The high levels of anti-α-GAL are an adaptive response to the ubiquitous presence of bacteria bearing α-GAL epitopes in the human digestive tract.

The most common tissue sources for xenographic bioprosthetic tissues are equine (horse), ovine (sheep), porcine (pig) and bovine (cow) tissues, all of which bear α-GAL epitopes and are potentially antigenic. One approach for limiting the antigenicity of bioprosthetic tissues is to chemically modify antigenic epitopes so that they are no longer recognized by host antibodies. This is typically accomplished by chemical fixation, which involves exposing a bioprosthetic tissue to a fixative agent (or tanning agent) that forms cross-linkages within (intramolecular cross-linkages) and/or between (intermolecular cross-linkages) polypeptides of the tissue. Examples of fixative agents used for treating bioprosthetic tissues include formaldehyde, glutaraldehyde, dialdehyde starch, hexamethylene diisocyanate and polyepoxy compounds. Glutaraldehyde is the most widely used fixative agent and glutaraldehyde treatment is currently the standard approach for stabilizing clinically useful bioprosthetic tissues. Examples of glutaraldehyde fixed bioprosthetic heart valves include the Carpentier-Edwards® Stented Porcine Bioprosthesis, the Carpentier-Edwards® PERIMOUNT® Pericardial Bioprosthesis, and the Edwards PRIMA Plus™ Stentless Aortic Bioprosthesis, all available from Edwards Lifesciences, Irvine, Calif. 92614.

Although chemical fixation can considerably limit the antigenicity of bioprosthetic tissues, fixed tissues, particularly glutaraldehyde-fixed tissue, suffer from several drawbacks. For example, the protective effects of glutaraldehyde fixation tend to deteriorate over the lifespan of bioprosthetic implants due to the labile Schiff Base cross-links, resulting in increased immunogenicity and impaired long-term stability and performance. In addition, glutaraldehyde treatment renders bioprosthetic tissues more susceptible to calcification, particularly when an implant remains in place for an extended period of time (e.g., more than ten years) due to their high levels of residual aldehyde groups. Structural valve deterioration (SVD) is the most common cause for early valve explanation, with tissue calcification the leading cause of failure in bioprosthetic implants. These glutaraldehyde-derived aldehydes are associated with high levels of calcium mineralization.

U.S. Pat. No. 6,861,211 to Levy and Vyavahare describes methods of stabilizing a bioprosthetic tissue through chemical cross-linking affected by treating the tissue with an agent, such as periodate, that oxidizes carbohydrate moieties of glycosaminoglycans (GAG) to generate aldehydes, and then treating the tissue with a bifunctional agent that reacts with the carbohydrate aldehydes as well as reactive groups on adjacent proteins to cross-link the GAG to the surrounding tissue matrix. Like conventional glutaraldehyde fixation, the methods result in residual reactive aldehyde groups, which serve as potential calcium binding sites and thus destabilize the tissue by ultimately compromising the biomechanical properties of the material.

U.S. Pat. No. 6,383,732 (Stone) describes an alternative to chemical modification for limiting the antigenicity of bioprosthetic tissues using the enzyme alpha-galactosiadase to destroy α-GAL epitopes. Enzymatic approaches suffer from the general high cost of enzyme preparations and the fact that the large size of alpha-galactosiadase and other enzymes prevents these protein structures from penetrating deeply into tissues, such as the extracellular matrix of pericardial bioprosthetic tissues. Thus, enzyme-based treatments do not eliminate all of the epitopes targeted by an enzyme, particularly in the interior of a bioprosthetic implant. In addition, alpha-galactosiadase and other enzymes are specific for particular epitopes (e.g., α-GAL in the case of alpha galactosiadase), making it highly difficult to limit the antigenicity of tissues containing multiple and/or unknown epitopes. The enzymatic removal of cellular components and tissue structures can also degrade the biomechanical properties of the tissue. Moreover, these enzyme treatments cannot be used with glutaraldehyde-fixed tissue since the enzyme's protein structure will react with the residual aldehydes and become covalently bound to the material. The result is an increase in foreign proteins and further degradation in tissue performance.

Accordingly, there remains a need in the art for the development of new and improved methods for reducing antigenicity and limiting calcification of xenographic tissues, thereby enhancing the durability, stability, and performance of the tissues. These enhanced characteristics are consistent with the demands of bioprosthetic tissues in vivo, including maintaining the structural, mechanical, and biocompatible properties of, for example, heart valves.

BRIEF SUMMARY

Methods are provided herein for improving the stability, durability, and/or performance of a xenographic bioprosthetic tissue implant by chemically modifying antigenic carbohydrates within the bioprosthetic tissue.

In some aspects, the methods comprise the steps of: treating the bioprosthetic tissue with an oxidizing agent which oxidizes vicinal diol moieties of antigenic carbohydrates to form aldehydes or acids and treating the bioprosthetic tissue with a capping agent, the capping agent comprising a primary amine or alcohol which combines with the aldehydes or acids to form imines, amides or esters.

In some aspects, the methods comprise the steps of: treating the bioprosthetic tissue with a capping agent, the capping agent comprising a primary amine or alcohol which combines with aldehydes or acids to form imines, amides or esters, and treating the bioprosthetic tissue with a stabilizing agent, the stabilizing agent converting the imines to secondary amines or the esters to amides.

In some aspects, the methods comprise the steps of: treating the bioprosthetic tissue with an oxidizing agent which oxidizes vicinal diol moieties of antigenic carbohydrates to form aldehydes or acids; treating the bioprosthetic tissue with a capping agent, the capping agent comprising a primary amine or alcohol which combines with the aldehydes or acids to form imines, amides or esters; and treating the bioprosthetic tissue with a stabilizing agent, the stabilizing agent converting the imines to secondary amines or the esters to amides.

In some aspects, the antigenic carbohydrate is N-glycolylneuraminic acid (Neu5Gc) in some aspects the antigenic carbohydrate is the Forssman antigen (GalNAc alpha1,3GalNAc beta1,3Gal alpha1,4Gal beta1,4Glc-Cer). In further aspects, the antigenic carbohydrate comprises an α-galactosyl (α-Gal) epitope.

In some aspects, the oxidizing agent is a periodate. In some aspects, the periodate selectively oxidizes vicinal diols of antigenic carbohydrates relative to β-aminoalcohol and/or vicinal diketone groups comprising the bioprosthetic tissue.

In some aspects, the capping agent is a primary amine. In further aspects, the primary amine reacts with aldehydes on the bioprosthetic tissue to form imines.

In some aspects, the capping agent is an alcohol. In further aspects, the alcohol reacts with acids on the bioprosthetic tissue to form esters.

In some aspects, the stabilizing agent is a reducing agent. In further aspects, the reducing agent converts bioprosthetic tissue imines to secondary amines and esters to amides.

In some aspects, the bioprosthetic tissue is treated with the oxidizing agent in the presence of the capping agent. In further aspects, the bioprosthetic tissue is washed sufficiently to remove the oxidizing agent prior to treatment with the reducing agent.

In some aspects, the bioprosthetic tissue is treated with the stabilizing agent in the presence of the primary amine or alcohol capping agent. In further aspects, the bioprosthetic tissue is treated with the capping agent and the stabilizing agent concurrently. In yet further aspects, the bioprosthetic tissue is washed to remove the oxidizing agent prior to treatment with the capping agent and/or the stabilizing agent.

In some aspects, the bioprosthetic tissue has been treated with one or more of a surfactant and/or a fixative agent. In various aspects, the fixative agent is selected from the group consisting of an aldehyde, a dialdehyde, a polyaldehyde, a diisocyanate, a carbodiimide, a photooxidation agent, and a polyepoxy compound and the surfactant is selected from the group consisting of an anionic surfactant, an alkyl sulfonic acid salt, a polyoxyethylene ether, a pluronic or tetronic surfactant, and an alkylated phenoxypolyethoxy alcohol.

In some preferred aspects, the bioprosthetic tissue has been treated with glutaraldehyde.

In some preferred aspects, the bioprosthetic implant is a heart valve. In further aspects, the bioprosthetic tissue is bovine pericardium or porcine aortic valve. In yet further aspects, the bioprosthetic implant is a pediatric heart valve.

In some aspects, the oxidized bioprosthetic tissue is substantially non-immunogenic in a human host. In further aspects, the antigenic carbohydrate of the treated bioprosthetic tissue is substantially non-antigenic in a human host. In yet further aspects, the treated bioprosthetic tissue is substantially non-calcifying in a human host. In some aspects, the human host is a pediatric patient.

In some aspects, the oxidizing agent is a periodate. In further aspects, the periodate is sodium periodate. In some aspects, the sodium periodate is used at a concentration of 20 mM. In some aspects, the bioprosthetic tissue is treated with sodium periodate for about 3 hours at about 25° C.

In some aspects, the method further comprises treating the bioprosthetic tissue with one or more of a surfactant and a fixative agent. In further aspects, the method comprises treating the bioprosthetic tissue with an aldehyde fixative agent. In yet further aspects, the method comprises treating the bioprosthetic tissue with glutaraldehyde. In some aspects, the fixative agent is carbodiimide (such as EDC). In some aspects, the fixative agent is diepoxy.

In some aspects, the bioprosthetic tissue is a fresh tissue.

In some aspects, the method further includes treating the bioprosthetic tissue with a bioburden reduction solution including formaldehyde, ethanol, and a Tween® solution. In some aspects, the method further includes drying the bioprosthetic tissue with ethanol and glycerol. In some aspects, the method further includes sterilizing the bioprosthetic tissue with ethylene oxide.

In some aspects, the method further includes decellularizing the bioprosthetic tissue with a decellularization method including treating the tissue with 0.1% SDS, rinsing the tissue, and treating the tissue with DNAse. In some aspects, the method further includes drying and electrophoretically cleaning the bioprosthetic tissue. In some aspects, the method further includes sterilizing the bioprosthetic tissue with glutaraldehyde.

In some aspects, the method further includes treating the bioprosthetic tissue with a bioburden reduction solution comprising ethanol and a Tween® solution.

Other aspects are described in co-owned U.S. Pub. No. 2009/0164005, filed Dec. 18, 2008, herein incorporated by reference in its entirety, for all purposes.

BRIEF DESCRIPTION OF THE DRAWINGS

As shown in FIG. 1, the process generally includes vicinal diol (i.e., vic Diol) oxidation, treatment with a capping agent, and/or treatment with a stabilizing agent.

FIG. 2 shows immunohistochemistry for α-Gal expression following treatments of un-fixed tissues. Blue is DNA (DAPI staining) and Green is α-Gal (Isolectin IB4 staining).

FIG. 3 shows immunohistochemistry for α-Gal expression on un-fixed tissues treated with various types of periodate. Stained areas are shown as lighter areas compared to the darker background. Blue is DNA (DAPI staining) and Green is α-Gal (Isolectin IB4 staining).

FIG. 4 shows that tissue fixed with glutaraldehyde has severe autofluorescence.

FIG. 5 also shows a flow-diagram of the process used for this experiment.

FIG. 7 also shows a flow-diagram of the process used for this experiment. Brown is α-Gal (Isolectin-IB4, DAB) and Blue is nuclei (Hematoxylin staining).

DETAILED DESCRIPTION

Figure 1:
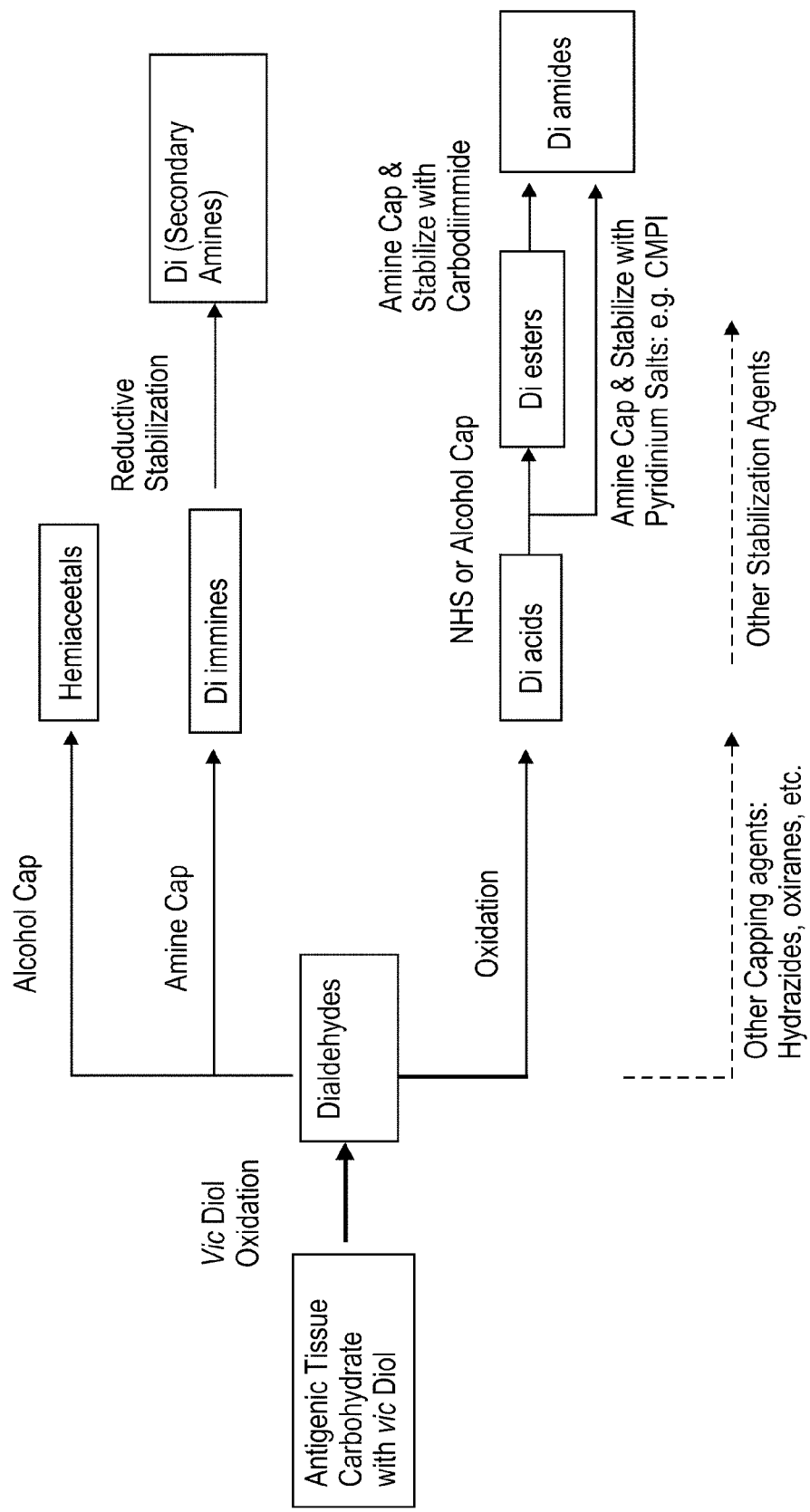
FIG. 1 shows various aspects of the tissue treatment process as provided in the present disclosure.

Descriptions of the invention are presented herein for purposes of describing various aspects, and are not intended to be exhaustive or limiting, as the scope of the invention will be limited only by the appended claims. Persons skilled in the relevant art can appreciate that many modifications and variations are possible in light of the aspect teachings.

Unless defined otherwise, all technical and scientific terms used herein have the meaning commonly understood by one of ordinary skill in the art. While exemplary methods and materials are described herein, it is understood that methods and materials similar or equivalent to those described can be used. All publications mentioned herein are incorporated by reference to disclose and describe the methods and/or materials in connection with which they are cited.

It must be noted that, as used in the specification, the singular forms "a", "an" and "the" include plural referents unless the context clearly dictates otherwise.

Methods are provided herein for mitigating the immunogenicity of a xenographic bioprosthetic tissue by chemically modifying one or more antigenic carbohydrates within the tissue while leaving the overall tissue structure substantially unmodified.

In some aspects, the methods comprise the steps of: treating the bioprosthetic tissue with an oxidizing agent which oxidizes vicinal diol moieties of antigenic carbohydrates to form aldehydes or acids and treating the bioprosthetic tissue with a capping agent, the capping agent comprising a primary amine or alcohol which combines with the aldehydes or acids to form imines, amides or esters.

In some aspects, the methods comprise the steps of: treating the bioprosthetic tissue with a capping agent, the capping agent comprising a primary amine or alcohol which combines with aldehydes or acids to form imines or esters, and treating the bioprosthetic tissue with a stabilizing agent, the stabilizing agent converting the imines to secondary amines or the esters to amides.

In some aspects, the methods comprise the steps of: treating the bioprosthetic tissue with an oxidizing agent which oxidizes vicinal diol moieties of antigenic carbohydrates to form aldehydes or acids; treating the bioprosthetic tissue with a capping agent, the capping agent comprising a primary amine or alcohol which combines with the aldehydes or acids to form imines or esters; and treating the bioprosthetic tissue with a stabilizing agent, the stabilizing agent converting the imines to secondary amines or the esters to amides.

Without being limited by a particular theory, it is believed that glutaraldehyde fixation and other established methods for stabilizing xenographic tissues suffer from several limitations that are associated with antigenicity, calcification, and long-term failure of bioprosthetic implants. Glutaraldehyde and other fixative agents stabilize tissues by forming cross-linkages between certain reactive moieties within the tissues without necessarily altering or eliminating antigenic epitopes. Glutaraldehyde fixation reduces antigenicity in a largely indirect manner due to the adsorption of host immune cells, antibodies, and serum proteins to concentrated aldehyde groups on the surfaces of glutaraldehyde fixed tissues, forming a coating of native molecules that isolates the tissue from host immune factors. However, such protein coatings deteriorate over time, exposing the tissue to the host immune system. In addition, the interior of glutaraldehyde fixed tissues often contains high levels of "latent antigens" due to the slow rate of penetration and diffusion of glutaraldehyde throughout treated tissues. As a result, glutaraldehyde fixed bioprosthetic tissues can become increasingly antigenic over time, leading to calcification, tissue fatigue, and eventually failure of the bioprosthetic implant.

Advantageously, methods provided herein reduce the antigenicity and/or calcification of bioprosthetic tissues by addressing one or more limitations associated with glutaraldehyde fixation and/or other established methods. Treating bioprosthetic tissues with periodate according to the instant methods selectively oxidizes antigenic carbohydrates, resulting in the covalent modification of xenographic antigens. In addition, periodate and other chemical agents are small molecules that readily diffuse throughout bioprosthetic tissues, including chemically fixed tissues, to eliminate latent antigens throughout the tissues. Methods provided herein use a capping agent to convert aldehyde groups produced by periodate oxidation and/or glutaraldehyde fixation to imines, and a reducing agent to convert the hydrolytically unstable imines to stable and substantially non-antigenic secondary amines. The methods thus eliminate reactive and toxic aldehydes and prevent further oxidation of aldehydes to acids that serve as potential calcium-binding sites. Moreover, calcification is further reduced by the modification of latent antigens and the resulting decreased immunogenicity of bioprosthetic tissues. Advantageously, methods provided herein improve the stability, durability, and/or performance of bioprosthetic tissue implants.

In some aspects, the "antigenic carbohydrate" targeted for modification by the instant methods is a glycosaminoglycan (GAG) polysaccharide that is found on glycoproteins and/or glycolipids of a xenographic tissue and is recognized as foreign by the immune system of a human subject. Antigenic carbohydrates within bioprosthetic tissues can trigger varying levels of immune responses that can decrease the performance, durability, and/or lifespan of the implant and potentially require immediate medical intervention to replace the implant. In some aspects, antigenic carbohydrates modified according to methods provided herein are "periodate labile" in that they comprise one or more exposed vicinal diol ($R^1$—CH(OH)CH(OH)—$R^2$) moieties capable of being oxidized by a periodate to produce a pendant aldehyde ($R^1$CHO). Advantageously, periodate oxidation of an antigenic carbohydrate modifies its structure so that it is no longer recognized by circulating antibodies. In some preferred aspects, treating a glutaraldehyde fixed tissue with periodate according to a method provided herein substantially eliminates periodate labile antigenic carbohydrate epitopes. In further aspects, treating a glutaraldehyde fixed tissue with periodate according to a method provided herein renders the tissue substantially non-antigenic.

In some aspects, an antigenic carbohydrate modified according to the instant methods is the α-GAL epitope (Galα$_{1-3}$Galβ$_{1-4}$GlcNAc—R). Treating an α-GAL-expressing xenographic tissue with periodate according to the methods provided herein results in oxidation of the vicinal diol of the α-GAL terminal galactose, producing two pendant aldehydes. The pendant aldehydes are preferably converted to imines by a primary amine-containing "capping agent", and the imines are converted to stable secondary amines by a reducing agent. Advantageously, periodate oxidation of the terminal galactose unit modifies the α-GAL epitope such that it is no longer recognized by human anti-α-GAL ("anti-GAL") antibodies, thus substantially reducing the antigenicity of the bioprosthetic tissue.

In further aspects, an antigenic carbohydrate modified according to the instant methods is the sialic acid N-glycolylneuraminic acid (Neu5Gc), the so called Hanganutziu-Deicher (HD) antigen, which comprises a nine-carbon sugar with a periodate labile vicinal diol. Neu5Gc is common in mammalian tissues, especially porcine tissues, but is not synthesized endogenously by humans. Nevertheless, Neu5Gc is sometimes detected at relatively stable levels in humans due to dietary intake and possible metabolic incorporation of small amounts of Neu5Gc in human glycoproteins. Human subjects have varying levels of circulating antibodies against Neu5Gc, with the highest levels comparable to those of anti-GAL antibodies. Advantageously, periodate oxidation of Neu5Gc sialic acid residues within a xenographic tissue modifies the Neu5Gc epitope so that it is no longer antigenic to human subjects.

In further aspects, the antigenic carbohydrate is the Forssman antigen (GalNAc alpha1,3GalNAc beta1,3Gal alpha1,4Gal beta1,4Glc-Cer). M. Ezzelarab, et al Immunology and Cell Biology 83, 396-404 (2005).

In some preferred aspects, treating a bioprosthetic tissue according to a method provided herein significantly reduces the antigenicity of the tissue in a human subject. In further aspects, treating a bioprosthetic tissue according to a method provided herein renders the tissue substantially non-antigenic in a human subject. In yet further aspects, methods provided herein significantly reduce antigenicity and/or render the tissue substantially non-antigenic in a human pediatric subject.

In some aspects, bioprosthetic tissues treated according to the instant methods have been treated with a fixative agent. As used herein, the terms "fixed" or "fixation" refer generally to the process of treating biological tissue with a chemical agent (a fixative agent) that forms intermolecular and intramolecular cross-linkages within and between structures in order to stabilize the tissue structure and prevent degradation. For example, fixation reduces the susceptibility of tissues to proteolytic cleavage by preventing the unfolding and denaturation required for proteases to access potential substrate proteins. Glutaraldehyde, formaldehyde, dialdehyde starch, and other aldehyde cross-linking agents are the most commonly used fixative agents for treating bioprosthetic tissues in preparation for surgical implantation. While fixation with fixative agents is desirable for stabilizing the tissue, fixation can also generate reactive chemical moieties in the tissue that are capable of binding calcium, phosphate, immunogenic factors, or other precursors to calcification. For example, glutaraldehyde fixation produces a high concentration of free aldehydes which are intrinsically toxic and can be further oxidized to form negatively charged carboxylic acid groups that serve as potential binding sites for positively charged calcium ions.

The term "calcification" as used herein, means deposition of one or more calcium compounds, such as calcium phosphate, calcium hydroxyapatite, and/or calcium carbonate, within a bioprosthetic tissue, which can lead to undesirable stiffening and/or degradation of the bioprosthesis. Although the precise mechanisms underlying calcification are unclear, calcification is generally known to arise in bioprosthetic tissues out of the interaction of plasma calcium ions with free aldehydes, phospholipids, and other tissue components. In addition, bioprosthetic tissues are particularly prone to calcification in pediatric subjects. Calcification can be intrinsic or extrinsic with respect to a bioprosthetic tissue. Intrinsic calcification is characterized by the precipitation of calcium and phosphate ions at sites within a bioprosthetic tissue, such as the extracellular matrix and remnant cells. Extrinsic calcification is characterized by the precipitation of calcium and phosphate ions on external sites on a bioprosthetic tissue by, e.g., thrombus formation or the development of surface plaques. Advantageously, methods provided herein reduce both intrinsic and extrinsic forms of calcification.

In some preferred aspects, treating a bioprosthetic tissue according to a method provided herein significantly reduces the level of calcification in the tissue and/or the propensity of the tissue for calcification in a human subject. In further preferred aspects, treating a bioprosthetic tissue according to a method provided herein renders the tissue substantially non-calcifying in a human subject. In yet further aspects, methods provided herein significantly reduce the level of and/or the propensity for calcification of a tissue and/or render a tissue substantially non-calcifying in a human pediatric subject.

The effects of the instant methods on reducing and/or eliminating xenographic antigens, free aldehydes, and/or calcification (or the propensity for calcification) can be detected using a variety of methods known to those skilled in the art. The mitigation of antigenic carbohydrates can be monitored by, e.g., direct galactose assays (α-GAL epitopes), immunohistochemical staining (e.g., using anti-α-GAL and/or anti-Neu5Gc antibodies), and conventional histology. The level of free aldehydes in a tissue can be measured spectrophotometrically using a colorimetric reagent, such as 4-amino-3-hydrazino-5-mercato-1,2,4-triazole (available under the tradename PURPALD), which reacts specifically with aldehydes to yield colored 6-mercapto-striazolo-(4,3-b)-s-tetrazines detectable at 550 nm, as described, e.g., in Dickinson and Jacobsen, Cem. Commun., 1719 (1970). A reduction in the concentration of free aldehydes in a bioprosthetic tissue can also be measured as a reduction in the toxicity of the tissue. For example, a bioprosthetic tissue (or sample thereof) can be used as a substrate for seeding cultured endothelial cells, and the growth of the endothelial cell monolayer on the bioprosthetic tissue substrate can provide a sensitive biological indicator of the number and concentration of residual aldehydes in the tissue.

The extent of calcification of a bioprosthetic tissue can be measured using a variety of methods known in the art, such as spectrophotometric methods (e.g., as described by Mirzaie et al., Ann. Thorac. Cardiovasc. Surg., 13:2 (2007)) and spectroscopic methods (e.g., inductively-coupled plasma mass spectroscopy (ICP-MS) after nitric acid ashing). Calcification of tissues may also be assayed by histological staining (e.g., Von Kossa staining) or by using a calcification indicator (e.g., eriochrome black T, murexide, or o-cresolphthalein, as described, e.g., in Sarkar et al., Anal Biochem, 20:155-166 (1967)). In addition, calcification of heart valve bioprosthetic implants can be detected by associated changes in the mechanical properties of the tissue, such as increased stiffening, which can be detected visually and/or measured using various methods known in the art. Those skilled in the art will be familiar with these and other methods.

As used herein, the term "bioprosthetic" refers to any prosthesis which is implanted in a mammalian subject, preferably a human subject, and derived in whole or in part from animal or other organic tissue(s). Bioprosthetic implants used in methods provided herein include tissue "patches," heart valves and other heart components, heart replacements, vascular replacements or grafts, urinary tract and bladder replacements, bowel and tissue resections, and the like.

Bioprosthetic implants treated according to methods provided herein can be derived from any biological tissue, including but not limited to, heart valves, blood vessels, skin, dura mater, pericardium, cartilage, ligaments and tendons. In some aspects, the tissue used to prepare a bioprosthetic implant is selected according to the degree of pliability or rigidity, which varies with the relative amounts of collagen and elastin present within the tissue, the structure and conformation of the tissue's connective tissue framework (e.g., arrangement of collagen and elastin fibers), and/or other factors known to those skilled in the art. Bioprosthetic tissues having relatively high levels of collagen, such as heart valve tissue and pericardial tissue, have been found to be particularly suitable for human bioprosthetic heart valve implant. However, those skilled in the art will realize that the instant methods can be used to treat bioprosthetic implants made from any suitable tissue.

In some preferred aspects, the bioprosthetic implant is a heart valve implant that is derived from a xenographic mammalian donor tissue and intended for use in a human subject. In further preferred aspects, the bioprosthetic implant is derived from a xenographic mammalian donor other than a great ape or an old world monkey, such as but not limited to, an equine donor, an ovine donor, a porcine donor or a bovine donor.

Those skilled in the art will recognize that the instant methods are particularly beneficial in treating those prostheses for which post-implantation degeneration and/or calcification poses a significant a clinical problem. For example, in some aspects, the bioprosthetic implant is a heart valve formed from bovine pericardium or porcine aortic valve and designed for implantation in a human subject. In yet further preferred aspects, the bioprosthetic implant is derived from a xenographic mammalian donor tissue and is designed for implantation in a human pediatric subject.

An "oxidizing agent" according to the present methods includes any mild oxidizing agent that is suitable for the selective oxidation of antigenic carbohydrates having vicinal diols to produce free aldehyde or acid moieties. Oxidizing agents according to the present disclosure can be halogen series oxidizing agents or peroxide series oxidizing agents or the like. Examples of oxidizing agents include, but are not limited to, periodic acid, salts of periodic acid such as sodium periodate, lead tetraaceatate, hydrogen peroxide, sodium chlorite, sodium hypochlorite, potassium permanganate, oxygen, halogens such as bromine and others known to those skilled in the art.

In some aspects, the oxidizing agent is a periodate. A "periodate" according to methods provided herein is a compound comprising a periodate ion ($IO_4^-$) that is capable of reacting, as shown in the reaction scheme below, with vicinal diol moieties (1) of antigenic carbohydrates to yield two pendant aldehyde moieties (2) along with formic acid and $H_2O$.

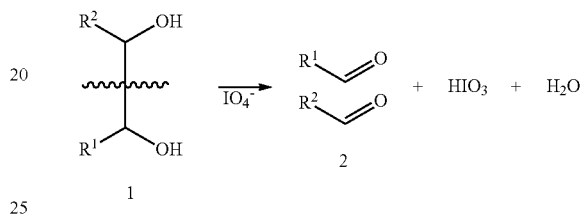

In some aspects, oxidation of vicinal diols is carried out in an aqueous solution, preferably an aqueous buffered solution, under conditions suitable for maintaining the structure and biological properties of the bioprosthetic tissue. In some aspects, a periodate is used for oxidation of vicinal diols. Typically, a stoichiometric amount of periodate is used to oxidize vicinal diol moieties, which amount can be determined empirically for a particular volume of tissue and/or for a particular type of tissue. Alternatively, a stoichiometric excess or periodate can be used. Solutions are generally buffered to have a pH between about 4 and about 9, with a pH between about 6 and about 8 desired for certain pH sensitive biomolecules. Periodate oxidation is generally carried out at a temperature between about 0 and about 50 degrees Celsius, and preferably at a temperature between about 4 and about 37 degrees Celsius. Depending on the antigenic carbohydrate(s) targeted for modification, the size and geometry of the bioprosthetic tissue and/or other considerations, periodate oxidation can be carried out for a period of between a few minutes to as long as many days. Preferably, periodate oxidation is carried out for a period between about several hours and about 24 hours. Long-term oxidation reactions are preferably performed under conditions that prevent over-oxidation. Treatment times and temperatures for periodate oxidation tend to be inversely related, in that higher treatment temperatures require relatively shorter treatment times. Those skilled in the art will recognize that the precise reaction conditions for a particular bioprosthetic tissue can be determined by routine experimentation, using methods known in the art.

In various aspects, the oxidizing agent is capable of oxidizing vicinal diols within antigenic carbohydrates targeted for modification, forming either pendant aldehyde moieties, which are converted to imines and then to more stable secondary amines by methods provided herein, or acids, which are converted directly to amides, or alternatively, converted to esters and then to more stable amides by methods provided herein. In some aspects, the size, charge, and/or other characteristics of the oxidizing agent allow it to readily penetrate and diffuse throughout the bioprosthetic tissue and be washed out of the tissue after a desired duration of treatment. In some aspects, the oxidizing agent is a periodate that is a periodic acid or a salt thereof, such as sodium periodate, potassium periodate, or another alkali metal periodate salt. In some preferred aspects, the oxidizing agent is sodium periodate. In some aspects the oxidizing agent is an acetate, such as lead acetate.

In some aspects, treating a bioprosthetic tissue with a periodate according to a method provided herein results in selective oxidation of vicinal diols relative to other reactive functionalities, including but not limited to, 2-aminoalcohols (e.g., on N-terminal serine, N-terminal threonine or 5-hydroxylysine residues), 1,2-aminothiols (e.g., on N-terminal cysteine residues), and vicinal diketones. In some preferred aspects, treating a bioprosthetic tissue with an oxidizing agent according to methods provided herein selectively oxidizes vicinal diols within one or more antigenic carbohydrates while leaving non-targeted structures substantially unmodified.

Without being limited to a particular theory, it is believed that potentially reactive moieties within bioprosthetic tissues vary in their susceptibility to oxidation with the following general order of reactivity (from most to least labile): vicinal diols, 2-aminoalcohols, 1,2-aminothiols, and vicinal diketones. In addition, the selectivity of an oxidizing agent for vicinal diols can be further enhanced by treating tissues with the oxidizing agent under mildly oxidizing conditions. Skilled artisans will recognize that mildly oxidizing conditions can be determined empirically using various methods known in the art, such as carrying out oxidation reactions under varying conditions with a mixture of carbohydrate substrates and monitoring the rate of production of reaction products. For example, the stringency of oxidation can be modulated by adjusting various reaction conditions, such as oxidizing agent concentration, treatment duration, temperature, solution chemistry, and the like.

In some aspects, a bioprosthetic tissue is treated with an oxidizing agent under conditions that favor oxidation of a particular antigenic carbohydrate. For example, antigenic carbohydrates having a sialic acid terminal sugar, such as Neu5Gc, are generally more susceptible to periodate oxidation than those having other terminal sugars, such as galactose (e.g., α-GAL).

In some aspects, the oxidizing agent selectively oxidizes vicinal diols of antigenic carbohydrates targeted for modification relative to other potentially labile moieties on biomolecules comprising the bioprosthetic tissue.

A "capping agent" according to the present methods includes any capping agent capable of reacting with free aldehyde or acid moieties. The capping agent can be a primary amine or an alcohol. In various aspects, the capping agent is $R^4$-M-NH$_2$, wherein: $R^4$ is H, $C_{1-6}$ alkyl, S(=O)$_2$OR$^5$, $C_{1-6}$ alkoxy, or hydroxyl; M is a linker, wherein the linker is $C_{1-6}$ alkylene; and $R^5$ is H or $C_{1-6}$ alkyl. In further aspects, $R^4$ is H. In yet further aspects, $R^4$ is S(=O)$_2$OR$^5$ and $R^5$ is H. In certain aspects, the capping agent is an amine, alkyl amine, hydroxylamine, aminoether, amino sulfonate, or a combination thereof.

Examples of capping agents include, but are not limited to, ethanolamine; taurine; amino acids such as glycine and lysine; alkoxy alkyl amines, such as 2-methoxyethylamine; n-alkyl amines such as ethylamine, and propylamine, N-Hydroxysuccinamide (NHS), N-Hydroxysulfosuccinamide (NHSS), and others known to those skilled in the art.

Chemical moieties referred to as univalent chemical moieties (e.g., alkyl, alkoxy, etc.) also encompass structurally permissible multivalent moieties, as understood by those skilled in the art. For example, while an "alkyl" moiety generally refers to a monovalent radical (e.g., CH$_3$CH$_2$—), in appropriate circumstances an "alkyl" moiety can also refer to a divalent radical (e.g., —CH$_2$CH$_2$—, which is equivalent to an "alkylene" group).

All atoms are understood to have their normal number of valences for bond formation (e.g., 4 for carbon, 3 for N, 2 for O, and 2, 4, or 6 for S, depending on the atom's oxidation state). On occasion a moiety can be defined, for example, as (A)$_a$B, wherein a is 0 or 1. In such instances, when a is 0 the moiety is B and when a is 1 the moiety is AB.

Where a substituent can vary in the number of atoms or groups of the same kind (e.g., alkyl groups can be $C_1$, $C_2$, $C_3$, etc.), the number of repeated atoms or groups can be represented by a range (e.g., $C_1$-$C_6$ alkyl) which includes each and every number in the range and any and all sub ranges. For example, $C_1$-$C_3$ alkyl includes $C_1$, $C_2$, $C_3$, $C_{1-2}$, $C_{1-3}$, and $C_{2-3}$ alkyl.

"Alkoxy" refers to an O-atom substituted by an alkyl group as defined herein, for example, methoxy (—OCH$_3$, a $C_1$alkoxy). The term "$C_{1-6}$ alkoxy" encompasses $C_1$ alkoxy, $C_2$ alkoxy, $C_3$ alkoxy, $C_4$ alkoxy, $C_5$ alkoxy, $C_6$ alkoxy, and any sub-range thereof.

"Alkyl" refer to straight and branched chain aliphatic groups having from 1 to 30 carbon atoms, or preferably from 1 to 15 carbon atoms, or more preferably from 1 to 6 carbon atoms, each optionally substituted with one, two or three substituents depending on valency. "Alkyl" includes unsaturated hydrocarbons such as "alkenyl" and "alkynyl," which comprise one or more double or triple bonds, respectively. The term "$C_{1-6}$ alkyl" encompasses $C_1$ alkyl, $C_2$ alkyl, $C_3$ alkyl, $C_4$ alkyl, $C_5$ alkyl, $C_6$ alkyl, and any sub-range thereof. Examples of such groups include, without limitation, methyl, ethyl, propyl, isopropyl, butyl, tert-butyl, isobutyl, pentyl, hexyl, vinyl, allyl, isobutenyl, ethynyl, and propynyl.

"Alkylene" refers to a divalent radical that is a branched or unbranched hydrocarbon fragment containing the specified number of carbon atoms, and having two points of attachment. An example is propylene (—CH$_2$CH$_2$CH$_2$—, a $C_3$alkylene). The term "$C_{1-6}$ alkylene" encompasses $C_1$ alkylene, $C_2$ alkylene, $C_3$ alkylene, $C_4$ alkylene, $C_5$ alkylene, $C_6$ alkylene, and any sub-range thereof.

"Amine" refers to a —N(R*)R** group, wherein R and R' are independently hydrogen, alkyl, alkenyl, alkynyl, aryl, aralkyl, cycloalkyl, heterocyclyl, or heteroaryl as defined herein. In the case of a primary amine, R* and R** are each H.

A "substituted" moiety is a moiety in which one or more hydrogen atoms have been independently replaced with another chemical substituent. As a non limiting example, substituted phenyl groups include 2-fluorophenyl, 3,4-dichlorophenyl, 3-chloro-4-fluorophenyl, and 2-fluoro-3-propylphenyl. In some instances, a methylene group (—CH$_2$—) is substituted with oxygen to form a carbonyl group (—CO).

An "optionally substituted" group can be substituted with from one to four, or preferably from one to three, or more preferably one or two non-hydrogen substituents. Examples of suitable substituents include, without limitation, alkyl, alkenyl, alkynyl, cycloalkyl, heterocycloalkyl, aryl, heteroaryl, aroyl, halo, hydroxy, oxo, nitro, alkoxy, amino, imino, azido, mercapto, acyl, carbamoyl, carboxy, carboxamido, amidino, guanidino, sulfonyl, sulfinyl, sulfonamido, formyl, cyano, and ureido groups.

Carboxylic acid groups like those in glutamic acid or gamma carboxy glutamic acid are known to bind calcium atoms. Calcium binding proteins such as bone sialoprotein contain carboxylic acid-rich domains designed to attract and bind calcium, leading to hydroxyapatite formation (calcification). The overall level and location of acid groups in these proteins determines the ability of the protein to efficiently bind calcium and form hydroxyapatite. The term "acid potential" of the tissue refers to the level of these chemical functional groups within the fixed tissue which may eventually form acid groups or "binding sites" by oxidation, dehydration, hydration, or similar processes.

Calcium binding causes significant post-implant damage in bioprosthetic materials, especially tissues used for heart valve leaflets. For example, the oxidative damage that occurs during storage and handling of dehydrated or "dry" tissue can create carboxylic acid groups that will bind calcium and lead to tissue failure. This progressive leaflet damage process can create new binding sites or potential binding sites that are precursors to calcification and immunogenic related pathways. The present disclosure provides for a method for capping these newly formed binding sites prior to implantation of the tissue for tissue-based bioprosthetic into the body. Bioprosthetic tissue exposed to oxidation from the atmosphere when not submersed in a glutaraldehyde solution or during sterilization is likely to contain more acid groups that contribute to calcification and inflammation. In dry storage, the dehydrated tissue is sterilized and stored "dry" without the protective effect of the glutaraldehyde solution. The ease of handling and storage of this new product is greatly facilitated due to the absence of the glutaraldehyde storage solution. This technology can be improved by treating such bioprosthetic tissue with a capping agent and/or adding a chemical protectant during the dehydration phase.

As shown in the reaction scheme below, a "capping agent" according to methods provided herein is in some aspects a primary amine ($R'NH_2$)-containing agent (3) capable of reacting with free aldehydes ($R^1CHO$) (2) to form imines ($R^3N=CHR^1$) (4).

Aldehyde Capping (Schiff base reaction):

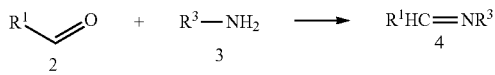

In some aspects, the capping reaction is carried out independently of oxidation in a neutral or slightly basic solution, at a temperature between about 0 and about 50 degrees Celsius, for a period of several minutes to many hours. Preferably, the reaction is carried out at a pH between about 6 and about 10, at a temperature between about 4 and about 37 degrees Celsius, and for a period of about 1 to about 3 hours. Those skilled in the art will recognize that the precise reaction conditions for a particular bioprosthetic tissue can be determined by routine experimentation, using methods known in the art.

One chemical target within the invention is the permanent "capping" of the acid groups which dramatically reduces their ability to attract calcium, phosphate, immunogenic factors, or other groups. The term "capping" refers to the blocking, removal, or alteration of a functional group that would have an adverse effect on the bioprosthesis properties. For example, the addition of 1-ethyl-3-[3-dimethylaminopropyl] carbodiimide hydrochloride (EDC), N-hydroxysulfosuccinimide (sulfo-NHS) and ethanolamine will effectively cap the acid groups with a non-reactive esters.

Preferably, the capping agent is capable of reacting with aldehydes or acids produced by oxidation of vicinal diols and/or by chemical fixation with an aldehyde fixative agent (e.g., glutaraldehyde) to form imines or esters under conditions suitable for maintaining the structure and function of the bioprosthetic implant. In various aspects, the capping agent can be an amine, an alkyl amine (e.g., ethylamine or isopropylamine), a hydroxyl amine (e.g., ethanolamine), an aminoether (e.g., 2-methoxyethylamine), an amino sulfonate (e.g., taurine, amino sulfates, dextran sulfate, or chondroitin sulfate), an amino acid (e.g., lysine or beta-alanine), a hydrophilic multifunctional polymer (e.g., polyvinyl alcohol or polyethyleneimine), hydrophobic multifunctional polymer (α-dicarbonyls, methylglyoxal, 3-deoxyflucosone, or glyoxal), a hydrazine (e.g., adipic hydrazide), mono-, di- or polyepoxy alkanes, or combinations thereof.

In some aspects, the capping agent is a monoamine. Without being limited by a particular theory, it is believed that certain agents comprising two or more primary amine groups can mediate cross-linking and other non-specific reactions within the bioprosthetic tissue. In some preferred aspects, the capping agent is selected from ethanaolamine, taurine (2-aminoethanesulfonic acid), 2-methoxyethylamine, and ethylamine. Advantageously, using a monoamine capping agent converts free aldehydes within a bioprosthetic tissue into stable secondary amines without forming residual reactive groups and/or altering the basic structural and/or mechanical properties of the tissue. Advantageously, using an alcohol capping agent such as ethanolamine, acids produced by oxidation of vicinal diols can be converted into stable esters without forming residual reactive groups and/or altering the basic structural and/or mechanical properties of the tissue.

In some aspects, the capping reaction is performed concurrently with vicinal diol oxidation to prevent sequential oxidation of aldehydes to carboxylic acids. The reaction can be carried out under essentially similar conditions as described above for oxidation. In further aspects, the bioprosthetic tissue is washed to remove the oxidation agent prior to treatment with the reducing agent.

In some preferred aspects, the bioprosthetic tissue is pre-treated with a chemical fixative agent, such as glutaraldehyde. Fixation limits potential cross-reactivity between aldehydes formed by oxidation and other reactive moieties within the tissue by extensively cross-linking the tissue and/or modifying reactive functionalities. For example, primary amines found on lysine and hydroxylysine residues of collagens and other proteins comprising the extracellular matrix can potentially compete with the capping agent in reactions with aldehydes formed by oxidation of vicinal diols and such competing reactions can have a negative impact on the structure and/or stability of the tissue. Chemical fixation with an aldehyde fixative agent, such as glutaraldehyde, substantially eliminates such competing reactions by cross-linking reactive amines within the tissue and stabilizing the overall tissue structure.

In some aspects, a bioprosthetic tissue is pre-treated with a protecting agent that couples to reactive moieties within the tissue and prevents undesired cross-linking and/or other reactions. For example, lysine amino acid residues may be protected or blocked by a number of methods known in the art, including but not limited to, the use of tert butyloxycarbonyl (Boc), benzyloxycarbonyl (Z), biphenylisopropyloxycarbonyl (Bpoc), triphenylmethyl (trityl), 9-fluoroenylmethyloxycarbonyl (Fmoc) protecting groups. Protecting groups may be preferred in cases where a bioprosthetic tissue is incompatible with chemical fixation, for example because of a need to preserve the native biological structure and/or activity of the tissue.

Advantageously, treating a fixed and/or oxidized bioprosthetic tissue with a capping agent according to the instant methods eliminates potential binding sites for calcium, phosphate, immune factors, and/or other undesirable factors. In further aspects, treating a bioprosthetic tissue with a capping agent according to the instant methods replaces aldehydes and/or acids within the tissue with a chemical moiety that imparts one or more beneficial properties to the tissue, such as a reduction in local and/or overall net charge, improved hemocompatibility, increased hydration, or improved mechanical flexibility. For example, treating a bioprosthetic tissue with the capping agent taurine replaces aldehydes with a sulfonate group which can be beneficial for tissue hydration, flexibility, and/or compatibility with host tissues. Furthermore, treating a bioprosthetic tissue with the capping agent ethanolamine replaces acids with ester moieties, thereby improving the biocompatibility of the tissue.

A "stabilizing agent" according to the present methods includes any chemical agent capable of reacting with free aldehyde or acid moieties. In various aspects, the stabilizing agents are reducing agents. The stabilizing agents are selected from the group consisting of sodium borohydride, sodium cyanoborohydride, lithium aluminum hydride, direct atmospheric or high pressure hydrogenation, carbodiimides such as 1-ethyl-3-(3-dimethylaminopropyl)carbodiimide (EDC), pyridines such as 2-chloro 1-methylpyridinium iodide (CMPI) and similar Mukaiyama's condensation reagents, and others known to those skilled in the art.

In some aspects, the present capping process can include chemical reduction of the tissue, which, when applied to the tissue in the presence of a capping agent, will permanently connect the capping agent to the target group. For example, the addition of ethanolamine to the tissue will cap the aldehyde groups, while the reducing agent (e.g., sodium borohydride) reduces any Schiff base created by reaction of the aldehyde with the amine group of ethanolamine. Thus an aldehyde is ultimately replaced by a stable chemical moiety, which may be beneficial for tissue hydration, flexibility, and cell interactions. Of course, other capping agents can be used instead of ethanolamine and other reducing agents other than sodium borohydride and are known by those skilled in the art and which are included in the scope of this patent. Another strategy provided by the present methods is to oxidize the tissue aldehydes to acids, and then cap the acid groups. This may involve the addition of 1-ethyl-3-[3-dimethylaminopropyl]carbodiimide hydrochloride (EDC), N-hydroxysulfosuccinimide (sulfo-NHS), or ethanolamine. These new "capped" groups will reduce the attraction of calcium, phosphate, immunogenic factors, or other similar agents.

In some aspects, the stabilizing agent is a reducing agent. A "reducing agent" according to methods provided herein is any agent capable of converting esters to amides or imines to secondary amines. In various aspects, the stabilizing agent is a reducing agent and can convert imines to secondary amines as shown in the reaction scheme below. As shown below, imines (4) produced by reaction of the capping agent with aldehydes (2) are reduced to form secondary amines (5) by using a suitable reducing agent.

Imine Reduction:

Imine reduction may be carried out under essentially the same conditions described above for the periodate oxidation and capping agent steps. In some aspects, imine reduction is carried out in a neutral or slightly basic solution, at a temperature between about 0 and about 50 degrees Celsius, and for a period of about a few minutes to many hours. Preferably, the pH is between about 6 and about 10, the temperature is between about 4 and about 37 degrees Celsius, and the reaction period is between about 3 to about 8 hours. In some aspects, the complete sequence of reactions is complete within about 24 hours.

The reaction of an aldehyde moiety ($R^1CHO$) with the primary amine moiety ($R^3NH_2$) of a capping agent produces a hemiaminal intermediate which forms the imine in a reversible manner through the loss of $H_2O$. In some aspects, the bioprosthetic tissue is treated with the capping agent separately from treatment with the reducing agent. The isolated imine reaction product is then converted to a secondary amine with a suitable reducing agent, such as but not limited to, sodium borohydride.

In some preferred aspects, the bioprosthetic tissue is treated with the reducing agent concurrently with the capping agent, such that imine formation and reduction of the hydrolytically unstable imine occur concurrently to form a secondary amine. In some preferred aspects, the bioprosthetic tissue is treated concurrently with the capping agent and a reducing agent that is selective for imines relative to aldehydes and/or ketones, such as but not limited to, sodium cyanoborohydride ($NaBH_3CN$), sodium triacetoxyborohydride ($NaBH(OCOCH_3)_3$), or a combination thereof.

In some aspects, aldehydes produced by oxidation and/or chemical fixation are reductively aminated directly, without formation of the intermediate imine, by treating a periodate oxidized bioprosthetic tissue with a reducing agent in an aqueous environment, e.g., as described in Dunsmore et al., J. Am. Chem. Soc., 128(7): 2224-2225 (2006).

In a particular aspect, an oxidation/capping and stabilization scheme is used involving the treatment of the tissue with a periodic acid salt to selectively cleave the vicinal diols of the carbohydrates, followed by treatment of the tissue with a secondary mild oxidizing agent such as sodium chlorite or hydrogen peroxide to convert the aldehydes to acids; then capping the acids with a capping agent selected from the group consisting of N-hydroxysuccinamide and N-hydroxysulfosuccinamide to form an ester; and then stabilizing the cap by converting the ester to an amide by the action of a carbodiimide stabilizing agent such as 1-ethyl-3-(3-dimethylaminopropyl)carbodiimide (EDC).

Also provided herein is a method for improving the performance of a bioprosthetic implant, the method including: obtaining the bioprosthetic tissue, wherein the bioprosthetic tissue is a fresh tissue; decellularizing the bioprosthetic tissue; fixing the bioprosthetic tissue with a fixation agent comprising glutaraldehyde; exposing the tissue to an initial bioburden reduction solution; at least partially fabricating a bioprosthetic product or device; treating the at least partially fabricated bioprosthetic tissue product or device with a second bioburden reduction solution comprising formaldehyde, ethanol, and a Tween® solution; treating the at least partially fabricating bioprosthetic product or device with a periodate, wherein the tissue expresses an antigenic carbohydrate including a vicinal diol, and wherein the vicinal diol is oxidized by the periodate to form an aldehyde; treating the bioprosthetic tissue with a capping agent, wherein the capping agent comprises a primary amine, and wherein the primary amine reacts with the aldehyde to form an imine; treating the bioprosthetic tissue with a reducing agent, wherein the reducing agent reacts with the imine to form a secondary amine;

drying the bioprosthetic tissue; and sterilizing the at least partially fabricated bioprosthetic product or device with ethylene oxide.

Also provided herein is a method for improving the performance of a bioprosthetic implant, the method including: obtaining the bioprosthetic tissue, wherein the bioprosthetic tissue is a fresh tissue; decellularizing the bioprosthetic tissue; fixing the bioprosthetic tissue with a fixation agent including glutaraldehyde; exposing the tissue to an initial bioburden reduction solution, at least partially fabricating a bioprosthetic tissue product or device; treating the at least partially fabricated bioprosthetic tissue product or device with a second bioburden reduction solution including formaldehyde, ethanol, and a Tween® solution; treating the at least partially fabricated bioprosthetic product or device with a periodate, the tissue expressing an antigenic carbohydrate including a vicinal diol, wherein the vicinal diol is oxidized by the periodate to form an aldehyde; treating the bioprosthetic tissue with a capping agent, wherein the capping agent includes a primary amine, wherein the primary amine interacts with the aldehyde to form an imine; treating the bioprosthetic tissue with a reducing agent, wherein the reducing agent interacts with the imine to form a secondary amine; drying and electrophoretically cleaning the bioprosthetic tissue; and sterilizing the at least partially fabricated bioprosthetic product or device with ethylene oxide.

Also provided herein is a method for improving the performance of a bioprosthetic implant, the method including: obtaining the bioprosthetic tissue, wherein the bioprosthetic tissue is a fresh tissue; decellularizing the bioprosthetic tissue; fixing the bioprosthetic tissue with a fixation agent including glutaraldehyde; exposing the tissue to an initial bioburden reduction solution; at least partially fabricating a bioprosthetic product or device; treating the at least partially fabricated bioprosthetic tissue product or device with a second bioburden reduction solution including formaldehyde, ethanol, and a Tween® solution; treating the at least partially fabricated bioprosthetic product or device with a periodate, the tissue expressing an antigenic carbohydrate including a vicinal diol, wherein the vicinal diol is oxidized by the periodate to form an aldehyde; treating the bioprosthetic tissue with a capping agent, wherein the capping agent includes a primary amine, wherein the primary amine interacts with the aldehyde to form an imine; treating the bioprosthetic tissue with a reducing agent, wherein the reducing agent interacts with the imine to form a secondary amine; drying and electrophoretically cleaning the bioprosthetic tissue; and sterilizing the at least partially fabricated bioprosthetic product or device glutaraldehyde.

Also provided herein is a method for improving the performance of a bioprosthetic implant, the method including: obtaining the bioprosthetic tissue, wherein the bioprosthetic tissue is a fresh tissue; decellularizing the bioprosthetic tissue; fixing the bioprosthetic tissue with a fixation agent including glutaraldehyde; exposing the tissue to an initial bioburden reduction solution; at least partially fabricating a bioprosthetic product or device; treating the at least partially fabricated bioprosthetic tissue product or device with a second bioburden reduction solution including formaldehyde, ethanol, and a Tween® solution; treating the at least partially fabricated bioprosthetic product or device with a periodate, the tissue expressing an antigenic carbohydrate including a vicinal diol, wherein the vicinal diol is oxidized by the periodate to form an aldehyde; treating the bioprosthetic tissue with a capping agent, wherein the capping agent includes a primary amine, wherein the primary amine interacts with the aldehyde to form an imine; treating the bioprosthetic tissue with a reducing agent, wherein the reducing agent interacts with the imine to form a secondary amine; drying and electrophoretically cleaning the bioprosthetic tissue; and sterilizing the at least partially fabricated bioprosthetic product or device drying and electrophoretically cleaning the bioprosthetic tissue; and sterilizing the bioprosthetic tissue with ethylene oxide.

In various aspects, bioprosthetic tissues subject to methods provided herein may be pre-treated with one or more secondary stabilizing agents, including but not limited to, a fixative agent and/or a skinning agent.

The instant methods are compatible with fresh, partially and fully fixed bioprosthetic tissues. Fixative agents useful for pre-treating bioprosthetic tissues used in methods provided herein include, but are not limited to, aldehydes (e.g., formaldehyde, glutaraldehyde, dialdehyde starch, acrolein, glyoxal acetaldehyde), polyglycidyl ethers (e.g., Denacol 810), diisocyanates (e.g., hexamethylene diisocyanate), carbodiimide(s), and epoxides (e.g., any of the various Denacols and their individual reactive species, including mono, di, tri, and multi-functionalized epoxides). In some preferred aspects, the bioprosthetic tissue has been previously fixed with glutaraldehyde, which has proven to be relatively physiologically inert and suitable for fixing a variety of biological tissues for subsequent surgical implantation (Carpentier, A., J. Thorac. Cardiovasc. Surg. 58:467-68 (1969)). An exemplary protocol for glutaraldehyde pre-treatment is set forth in Example 1. Fixation with glutaraldehyde or another fixative agent can provide a variety of benefits, including increased stability, increased durability, improved preservation, increased resistance to proteolytic cleavage.

In some aspects, the bioprosthetic implant is a commercially available bioprosthetic heart valve, such as the Carpentier-Edwards® stented porcine bioprosthesis, Edwards Lifesciences, Irvine, Calif., the Carpentier-Edwards® Pericardial Bioprosthesis, Edwards Lifesciences, Irvine, Calif., or the Edwards® PRIMA Stentless Aortic Bioprosthesis, Edwards Lifesciences AG, Switzerland, which has been treated according to a method provided herein.

In further aspects, the bioprosthetic tissue is a fresh, non-fixed xenographic tissue harvested from a mammalian host, which is treated according to methods provided herein and implanted into a host subject.

The tissue to be treated can be freshly harvested from an abattoir, it can be washed and pre-treated with various decellurizing agents, and/or it can be at least partially fixed with fixative agents. After the stabilization step, the tissue can also be treated by decelluarization methods, various fixation methods, bioburden reduction, drying and glycerolization, and final sterilization steps. It is understood that in general some or all of the sequential steps can be combined into simultaneous steps e.g., the oxidation and capping step, the capping and stabilization steps, or all three steps can react in concert. Likewise some or all of the pre- and post-carbohydrate antigen mitigation steps can be combined into a smaller set of various simultaneous steps.

A number of surfactants may be used in accordance with the present methods, including but not limited to, anionic surfactants (e.g., esters of lauric acid, including but not limited to, sodium dodecyl sulfate), alkyl sulfonic acid salts (e.g., 1-decanesulfonic acid sodium salt), non-ionic surfactants (e.g., compounds based on the polyoxyethylene ether structures, including Triton X-100, 114, 405, and N-101 available commercially from Sigma Chemical, St. Louis, Mo., and related structures, and pluronic and tetronic surfactants, available commercially from BASF Chemicals, Mount Olive, N.J.), alkylated phenoxypolyethoxy alcohols (e.g., NP40, Nonidet P40, Igepal, CA630, hydrolyzed/functionalized animal and plant compounds including, Tween® 80, Tween® 20, octyl-derivatives, octyl b-glucoside, octyl b-thioglucopyranoside, deoxycholate and derivatives thereof, zwitterionic compounds, 3-([cholamidopropyl]-dimethyl ammonio-1-propanesulfonate (CHAPS), 3-([cholamidopropyl]-dimethyl ammonio)-2-hydroxy-1-propanesulfonate (CHAPSO)), and mixtures thereof (e.g., deoxycholate/Triton, Micro-80/90).

In some aspects a tissue is treated with a cell disrupting agent. Cell disrupting agents can include a hypotonic saline of 0% to 0.5% NaCl, non-ionic, anionic, and/or cationic detergents, and surfactants, e.g., Tweens, sodium dodecyl sulfate (SDS), sodium deoxycholate, tetradecyl ammonium chloride, and benzalkonium chloride. In one aspect, CHAPSO in the range of 0% to 5% can be used as a cell disrupting agent.

In some aspects a tissue is treated with a proteolytic inhibitor including, e.g., Protinin or EDTA.

In some aspects a tissue is treated with a lipid, phospholipid, cell membrane, and/or cell remnant extracting agent. Such extracting agents can include alcohols (e.g., ethanol, 2-propanol, or n-decanol in the concentration range of 1% to 100%); ketones (e.g., acetone, methyl ethyl ketone); ethers (e.g., diethyl ether, tetrahydrofurane, 2-methoxy ethanol); surfactants and detergents (e.g., Tweens®, sodium dodecyl sulfate (SDS), sodium deoxycholate, tetradecyl ammonium chloride, benzalkonium chloride); CHAPSO; or Supercritical fluids (e.g., $CO_2$, NO).

In some aspects a tissue is treated with an anti-antigenic enzyme (e.g., DNAse, RNAse).

In some aspects a tissue is treated with a bioburden reducing agent, including: antibiotics (e.g., penicillin, streptomycin); alcohols (e.g., ethanol, 2-propanol, n-decanol in the concentration range of 1% to 100%); aldehydes (e.g., formaldehyde, acetaldehyde, glutaraldehyde in the range of 0% to 5%).

In one aspect, a tissue is treated with a bioburden reducing solution that is a combination of formaldehyde, ethanol, and Tween® 80 (FETs) in a concentration of about 1%/22.5%/0.1%, respectively.

In some aspects, a fabrication device is used for at least partially fabricating a bioprosthetic product or device. The fabrication device can be any device that is suitable for the assembly of a bioprosthetic product or device.

Those skilled in the art will appreciate that various alternative agents suitable for pre-treating bioprosthetic tissues are known in the art and may be substituted for those indicated herein.

Having now generally described the invention, the same will be more readily understood through reference to the following examples which are provided by way of illustration, and are not intended to be limiting of the disclosed invention, unless specified.

EXEMPLARY ASPECTS

Example 1

Tissue Pre-Treatment

Prior to chemically modifying the antigenic carbohydrates in a xenographic bioprosthetic tissue, the tissue may optionally be pre-treated by exposure to cross-linking agents and/or surfactants. The following non-limiting procedure sets forth one potential tissue pre-treatment protocol that produces fixed tissues. Those skilled in the art will appreciate that various alternative methods, chemical compounds, or solutions may be substituted for those indicated.

Step 1: Harvest/Prepare Biological Tissue

A desired biological tissue is harvested (surgically removed or cut away from a host animal) at a slaughterhouse, placed on ice, and transported to the location at which the bioprosthesis will be manufactured. Thereafter, the tissue is typically trimmed and washed with a suitable washing solution, such as a saline solution, sterile water, or a basic salt solution. For example, harvested tissues can be rinsed, washed, and/or stored in a phosphate or non-phosphate buffered saline solution that includes an organic buffering agent suitable for maintaining the solutions at a physiologically compatible pH without deleterious effects to the tissue. Both phosphate and non-phosphate buffering agents are suitable for tissue processing. The following buffering agents, at a concentration of about 10 mM to about 30 mM, are generally suitable for non-phosphate buffered saline solutions used herein: acetate, borate, citrate, HEPES (N-2-hydroxyethylpiperazine-N'-2-ethanesulfonic acid), BES (N,N-bis[2-hydroxyethyl]-2-amino-ethanesulfonic acid), TES (N-tris[hydroxymethyl]methyl-2-aminoethanesulfonic acid), MOPS (morpholine propanesulfonic acid), PIPES (piperazine-N,N'-bis[2-ethane-sulfonic acid]), or MES (2-morpholino ethanesulfonic acid). The buffering agent HEPES, which has a pKa of about 7.4, is well-suited for tissue processing. Advantageously, the use of a non-phosphate buffered organic saline solution typically decreases the likelihood of calcium precipitation on a bioprosthetic tissue.

Buffered saline solutions used in the instant methods may also comprise a chelating agent, which preferably binds divalent cations, such as calcium, magnesium, zinc, and manganese. Examples of suitable chelating agents include EDTA (ethylenediaminetetraacetic acid), EGTA (ethylenebis(oxyethylenenitrilo)tetraacetic acid), ethylenebis(oxyethylenenitrilo)tetraacetic acid, citric acid or salts thereof, and sodium citrate, at concentrations of about 20 mM to about 30 mM. Advantageously, the removal of divalent cations by the chelating agent renders the tissue less susceptible to spontaneous precipitation of the divalent ions with phosphate ions that may be present in the tissue.

In one aspect, the non-phosphate buffered organic saline solution is isotonic and comprises about 0.9 wt-% saline, about 10 mM to about 30 mM HEPES buffer, pH 7.4, and about 20 mM to about 30 mM of EDTA.

Step 2: Glutaraldehyde Fixation of Biological Tissue

The harvested, trimmed and washed tissue is disposed within a container filled with a 0.625% solution of glutaraldehyde comprising approximately 26 ml/l glutaraldehyde (25%); approximately 4.863 g/l HEPES buffer; approximately 2.65 g/l $MgCl_2.6H_2O$; and approximately 4.71 g/l NaCl. The balance of the solution comprises double filtered $H_2O$, NaOH is added to adjust the pH to approximately 7.4. The glutaraldehyde solution can optionally contain a sterilant (e.g., 2% (w/w) ethanol) and/or a skinning agent (e.g., 1% (w/w) Tween® 80). Where the glutaraldehyde solution contains a sterilant and/or skinning agent, the tissue is incubated at a controlled temperature (e.g., between about 20 to 37° C.) with continuous circulation of the solution for a period of between about 2 to 24 hours, typically about 9 hours. The tissue is then washed and incubated in glutaraldehyde solution without sterilant or skinning agent at a controlled temperature (e.g., 50+/−5° C.) with continuous circulation for a period of between about 7 to 14 days to complete glutaraldehyde fixation. Room air is allowed to blanket or cover the glutaraldehyde solution throughout the process. Glutaraldehyde fixed tissues prepared according to the instant methods are preferably fixed under conditions that allow the tissues to be immersed in 6N hydrochloric acid at 110° C. for 5 days with minimal degradation.

Step 3: Assembly/Fabrication of Prosthesis

After completion of Steps 1 and 2, the tissue is rinsed with a suitable rinsing solution such as buffered saline or 0.625% glutaraldehyde. Thereafter, the tissue may be transported into a clean room or aseptic environment, further trimmed or shaped (if necessary) and assembled with any non-biological components (e.g., stents, frames, suture rings, conduits, segments of polyester mesh to prevent suture tear-through, etc.) to form the desired implantable bioprosthetic device.

Example 2

Selective Chemical Modification of Antigenic Carbohydrates

Chemical modification of antigenic carbohydrates in a xenographic bioprosthetic tissue, as described herein, may be performed whether or not the tissue is pre-treated. The following non-limiting procedure sets forth methods for chemically modifying select antigenic carbohydrates in either scenario.

After the bioprosthetic tissue has been rinsed and stored, the tissue is preferably immersed in isotonic buffered saline solution containing a periodate oxidizing agent, such as sodium periodate, at a concentration of about 20 mM for a period of about 20 minutes at room temperature with constant agitation.

After treatment with the periodate oxidizing agent, the tissue is rinsed extensively in 20% ethanol to completely remove the periodate, preferably in a vessel allowing a large solution to tissue volume ratio to create a favorable gradient for solute diffusion.

The tissue is then immersed in a solution containing a primary amine capping agent and a reducing agent suitable for converting any free aldehydes within the tissue to secondary amines. In one method, the tissue is immersed in isotonic buffered saline solution with a pH of 8.5 containing a capping/reducing solution comprised of taurine and isoproplyamine 50%/50% 20 mM and 10 mM sodium borohyride at room temperature for a period of about 10 minutes with constant agitation. The tissue is then washed and treatment with the capping/reducing solution is repeated for a total of three 10 minute treatments with the capping/reducing solution.

The bioprosthetic tissue is removed from the capping/reducing agent solution, rinsed in 20% ethanol, and transferred to a container and fully immersed in a phosphate-buffered storage solution comprising 0.25% glutaraldehyde, formaldehyde, ethanol, and Tween® (pH adjusted to 7.4 with HCl and NaOH). Thereafter, the container is sealed and placed in an oven where it is heated to a terminal sterilization temperature of 37.5+/-2.5° C. for 25 to 27 hours. The container is then cooled to room temperature and stored until the time of implantation.

Example 3

Treatment of Un-Fixed Tissue with Periodate

Tissue Treatment

Bovine pericardial tissue (National Beef, Item #192769001, WO#58745266) was treated to mask antigens by the following procedure. Tissue was soaked in a phosphate buffer containing 10 mM ethanolamine (Alfa Aesar, #36260) with pH 7.0±0.5 or 10 mM taurine with 7.0±0.5 pH (Sigma, #T0625). In both treatment groups, sodium periodate (Sigma, #311448) was added to yield a 20 mM solution with 7.0±0.5 pH. Tissue from the two groups was incubated in one of three ways: 1) shaking at 4° C. for 18 hours (New Brunswick Scientific, Innova 4230, refrigerated incubator/shaker) 2) shaking at room temperature for 3 hours (VWR, Model 1000, orbital shaker) and 3) shaking at 37° C. for 30 min. (VWR, Model 1570, orbital shaker/incubator). After treatment the tissue was rinsed thoroughly in 0.9% saline (Baxter, #2F7124). The tissue was then incubated in ethanolamine and sodium borohydride (Sigma, #452882) for 1 hour at room temperature while shaking. Once again tissue was rinsed thoroughly in saline. One piece of tissue was placed in 10% Neutral Buffered Formalin (Lazer Scientific, NBF-4G) the remaining tissue was frozen in liquid nitrogen and stored at −80° C. for future analysis.

Histochemical Procedure

Tissue samples from each group were processed according to standard paraffin embedding procedure. Tissue was fixed overnight in neutral buffered formalin. Tissue was then dehydrated through a series of graded alcohol (Harleco, #65347); 70%, 80%, 95% and 100% and cleared in xylene (EMD Sciences, #XX0060-4) before being embedded in paraffin wax (McCormick Scientific, Para-Plast Plus #502004) using histology tissue processor (Sakura, Tissue-Tek VIP-1000). Each sample was then embedded into a wax block (Miles Scientific embedding station) and sectioned at ~5 µm using a rotary microtome (Reichert, HistoStat). The resulting slides (Fisher, #15-188-51) were heat-fixed overnight before staining.

Tissue from each slide was stained with standard H&E procedure and immunohistochemistry, for the presence of α-galactose. Paraffin was removed by incubating in Xylene and rehydrated through a series of graded alcohol; 100%, 95% 80% and water. For H&E, slides were stained with Gill modified hematoxylin (Harleco, #65065), followed by staining in Eosin Phloxine (ENG Scientific, #8923). After staining, slides were dehydrated and mounted (Fisher permount, #SP-15). Slides for immunohistochemistry were incubated in isolectin-GS $IB_4$ conjugated to Alexa Fluor 488 (1:500, Invitrogen, I21411) in PBS, for 2 hrs at 37° C.

Results

Figure 2B:
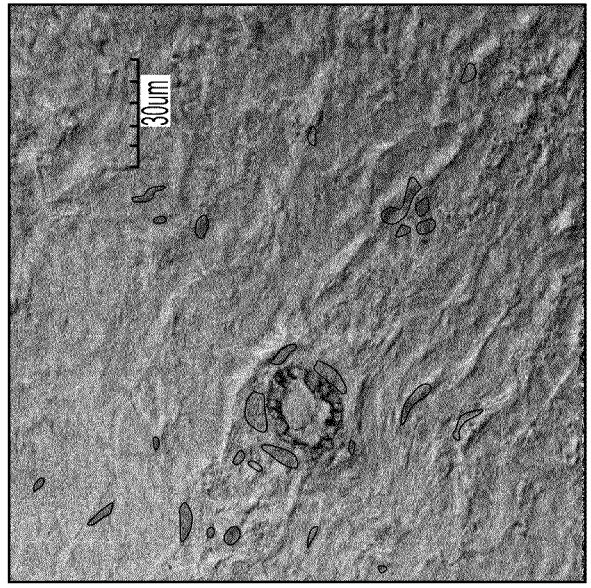
FIG. 2B shows a lighter area of intense α-Gal (Isolectin IB4 staining) in fresh, un-fixed tissue treated with periodate only.
Figure 2A:
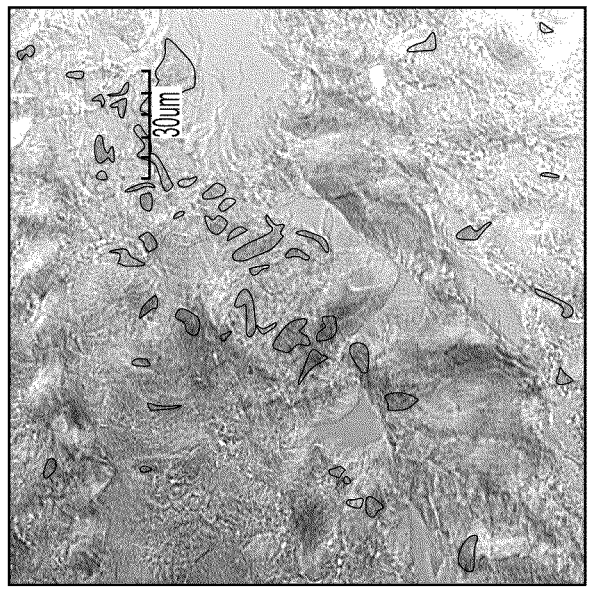
FIG. 2A shows minimal staining in fresh, un-fixed tissue treated with the process described herein (vic Diol oxidation, capping agent, and reducing agent).

Fresh, unfixed tissue was subjected to periodate treatments, with or without treatment according to the methods described herein (oxidizing agent such as periodate, capping agent, and reducing agent). FIG. 2 shows immunohistochemistry for α-Gal expression following NexGen treatments of un-fixed tissues. FIG. 2A shows fresh, un-fixed tissue treated according to the methods described herein. FIG. 2B shows fresh, un-fixed tissue treated with periodate only. The combined treatment of fresh, unfixed tissues according to the methods described herein completely inhibits the binding of α-Gal antibody to the tissue compared to control tissue treated with periodate only.

Figure 3B:
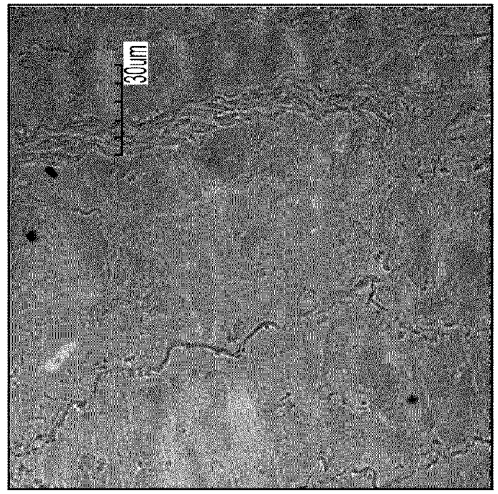
FIG. 3B shows un-fixed tissue treated with a commercially available decellularized collagen tissue.
Figure 3A:
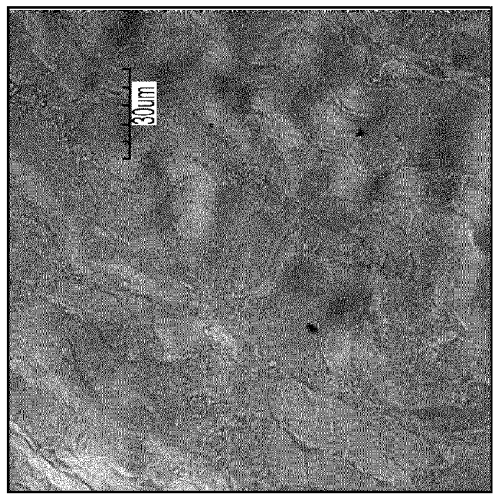
FIG. 3A shows un-fixed tissue treated with a 1% SDS/DNAse decellularization procedure.
Figure 3C:
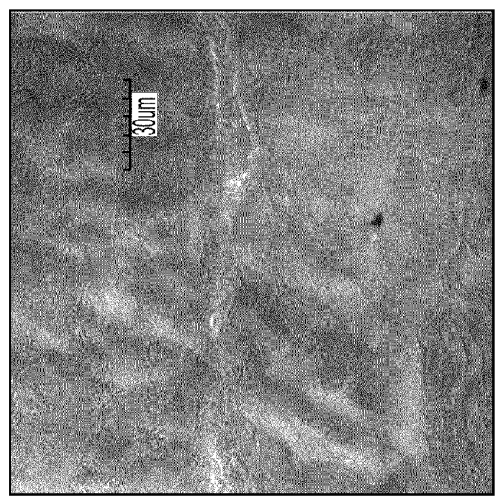
FIG. 3C shows un-fixed tissue treated with another commercially available decellularized collagen tissue.

FIG. 3 shows immunohistochemistry for α-Gal expression on un-fixed tissues treated with various types of periodate solutions. FIG. 3A shows un-fixed tissue treated with an in-house decell periodate. FIG. 3B shows un-fixed tissue treated with a Lifenet decell periodate. FIG. 3C shows un-fixed tissue treated with another commercial decell periodate.

Example 4

Treatment of Fixed Tissue with Periodate

Tissue Treatment

Thermafix (tissue fixation followed by heat treatment; TFX) treated pericardial tissue was obtained from isolation.

Tissue was rinsed in three changes of 0.9% saline (Baxter, #2F7124) before being soaked in a phosphate buffer containing 10 mM ethanolamine (Alfa Aesar, #36260) and 20 mM sodium periodate (Sigma 311448) or 10 mM taurine (Sigma, #T0625) with 20 mM sodium periodate. Tissue from the both groups was incubated at room temperature for 3 hours while shaking (VWR, Model 1000, orbital shaker). After treatment the tissue was rinsed thoroughly in 0.9% saline. The tissue was then incubated in 0.06% ethanolamine and 0.25% sodium borohydride (Sigma, #452882) for 1 hour at room temperature while shaking. Once again tissue was rinsed thoroughly in saline. Tissue from each group was stored in 0.625% glutaraldehyde (EW #400611) and the remaining tissue was incubated in 75% glycerol (JT Baker, #4043-01)/25% ethanol (EMD, #EX0276-3) for one hour at room temperature. Tissue was then laid out on absorbent pads to remove excess glycerol solution. One piece from each group was placed in 10% Neutral Buffered Formalin (Lazer Scientific, NBF-4G).

Histochemical Procedure

Tissue samples from each group were processed according to standard paraffin embedding procedure. Tissue was fixed overnight in neutral buffered formalin. Tissue was then dehydrated through a series of graded alcohol (Harleco, #65347); 70%, 80%, 95% and 100% and cleared in xylene (EMD Sciences, #XX0060-4) before being embedded in paraffin wax (McCormick Scientific, Para-Plast Plus #502004) using histology tissue processor (Sakura, Tissue-Tek VIP-1000). Each sample was then embedded into a wax block (Miles Scientific embedding station) and sectioned at ~5 µm using a rotary microtome (Reichert, HistoStat). The resulting slides (Fisher, #15-188-51) were heat-fixed overnight before staining.

Tissue from each slide was stained with standard H&E procedure and immunohistochemistry, for the presence of a-galactose. Paraffin was removed by incubating in Xylene and rehydrated through a series of graded alcohol; 100%, 95% 80% and water. For H&E, slides were stained with Gill modified hematoxylin (Harleco, #65065), followed by staining in Eosin Phloxine (ENG Scientific, #8923). After staining, slides were dehydrated and mounted (Fisher permount, #SP-15). Slides for immunohistochemistry were incubated in solutions according to typical immunohistochemical staining with PBS (GBiosciences, #R028) rinses in between each step; 3% hydrogen peroxide (Sigma, #216763) in methanol (EMD, #MX0475P-1) for 15 minutes, 1% albumin, bovine serum (BSA, Sigma #A7030) in PBS with Tween® 20 (VWR, BDH4210) for 30 minutes, isolectin-GS $IB_4$ conjugated to biotin (1:2000, Invitrogen, 121414) in PBS for 1 hr at room temperature, Vectastain ABC reagent (Vector Laboratories, PK-1600) for 30 minutes and diamino-benzidine (DAB) reagent kit (KPL #54-10-00) for less than 3 minutes. Tissue was counterstained with Hematoxylin (Harleco, #65065) for 1 minute and dehydrated in alcohol series before mounting in permount (Fisher, SP-15).

Results

Fixed tissue was subjected to TFX, with or without treatment with periodate and/or capping with sodium borohydride and either ethanolamine or taurine.

FIG. 4 shows that tissue fixed with glutaraldehyde has severe autofluorescence. The tissue shown was treated with TFX and periodate. Isolectin dye was used for staining.

Figure 5:
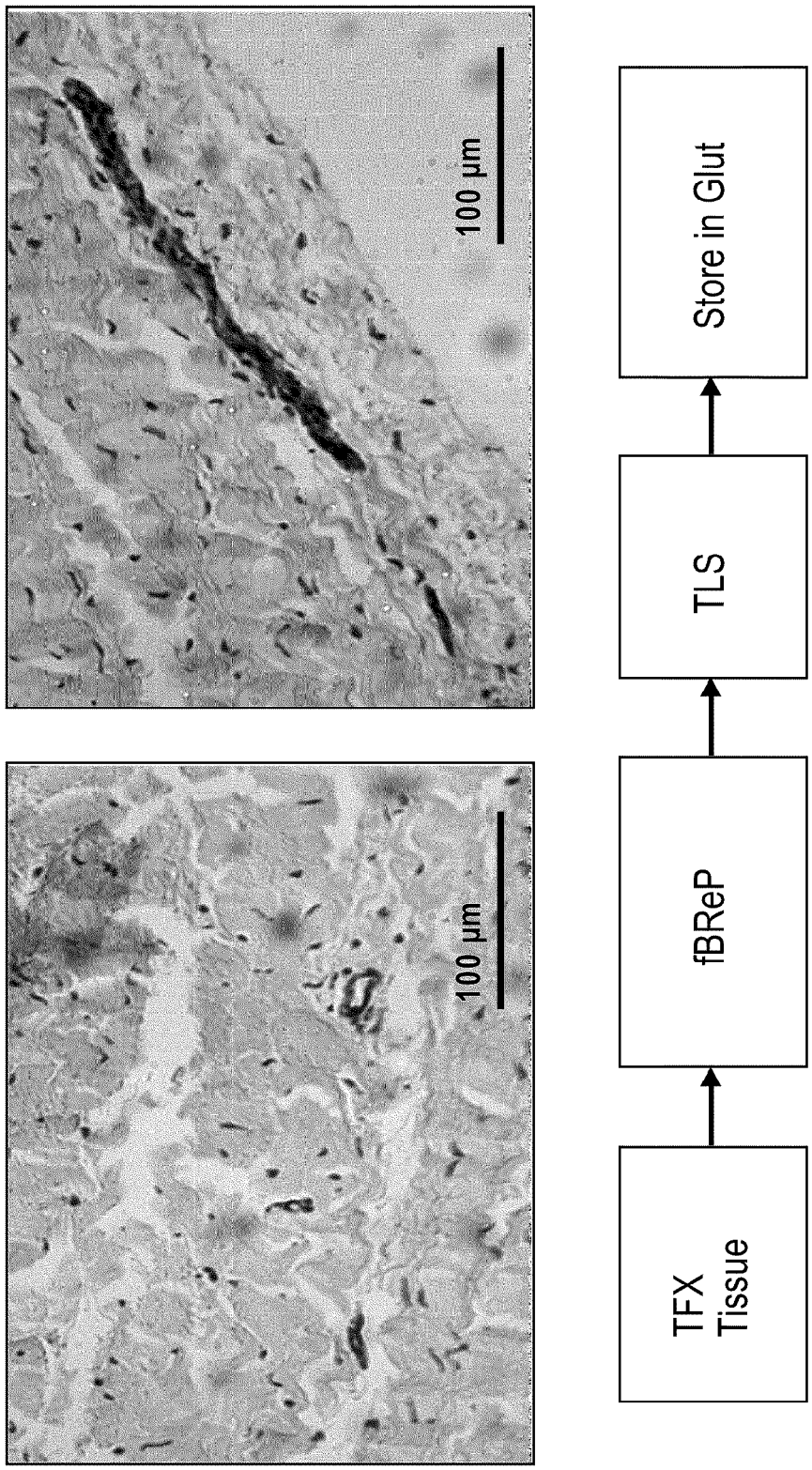
FIG. 5 shows α-Gal and DNA expression as darker areas on fixed tissue treated with ThermaFix (TFX) only. Brown is α-Gal (Isolectin-IB4, DAB) and Blue is nuclei (Hematoxylin staining).

TFX tissue was treated with formaldehyde bioburden reduction process (fBReP), then terminal liquid sterilization (TLS), and then stored in glutaraldehyde. FIG. 5 shows α-Gal and DNA expression on fixed tissue treated with TFX only. FIG. 5 also shows a flow-diagram of the process used for this experiment, also described above. The presence of brown staining demonstrates the inability of TFX treatment alone to block the binding of α-Gal antibody to the fixed tissue.

Figure 6:
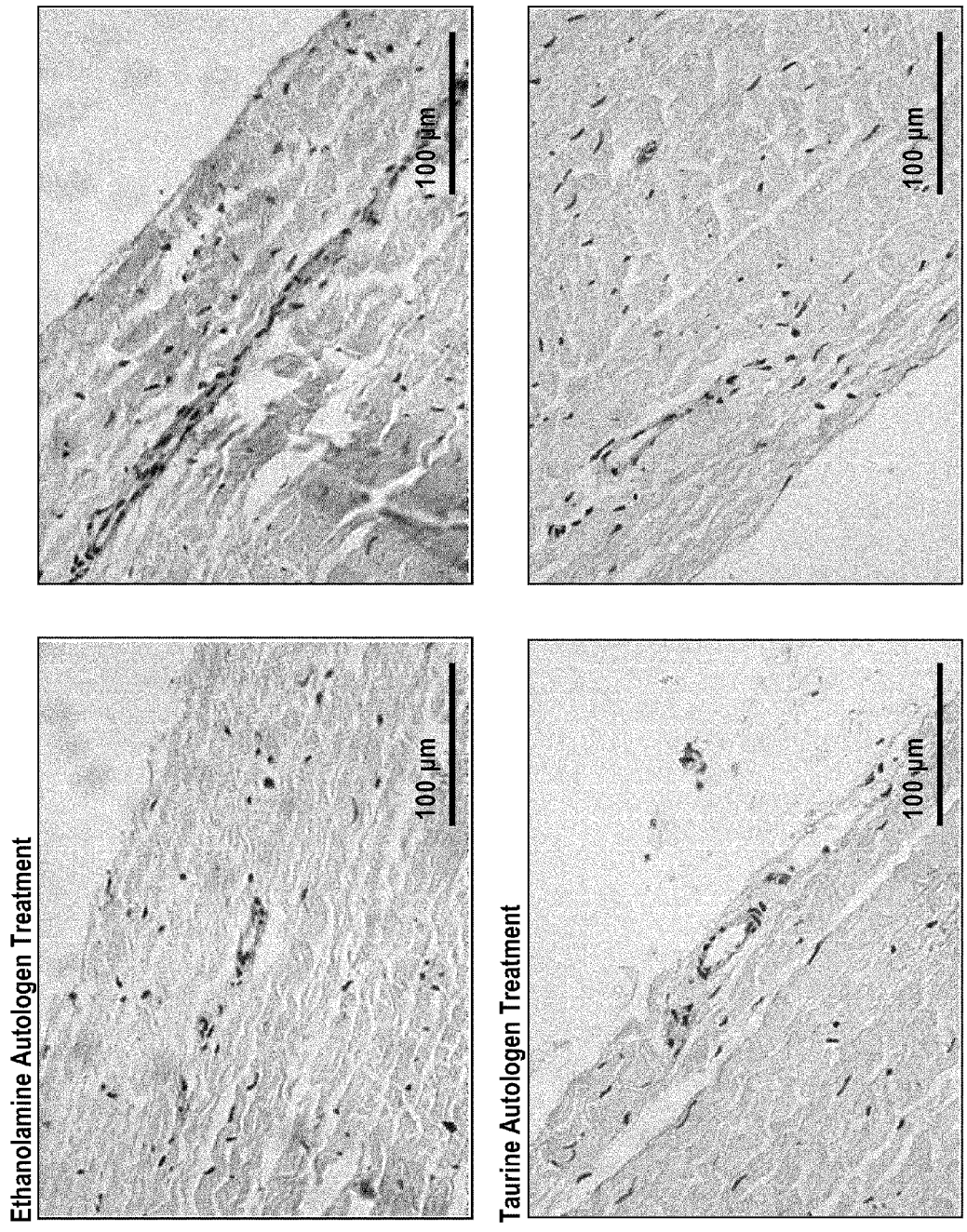
FIG. 6 shows α-Gal and DNA expression as darker areas on fixed tissue treated with the combined treatment of fixed tissue with TFX and the process described herein. The upper panels show tissue treated with ethanolamine. The lower panels show tissue treated with taurine. Brown is α-Gal (Isolectin-IB4, DAB) and Blue is nuclei (Hematoxylin staining).

TFX/fBReP tissue was subjected to periodate treatment followed by capping and then stored in glutaraldehyde. FIG. 6 shows the combined treatment of fixed tissue with TFX and periodate, a capping agent, and a reducing agent. The upper panels show tissue treated with ethanolamine as the capping agent. The lower panels show tissue treated with taurine as the capping agent. The absence of brown staining demonstrates the inability of α-Gal antibody to bind the fixed tissue following the combined treatment.

Figure 7:
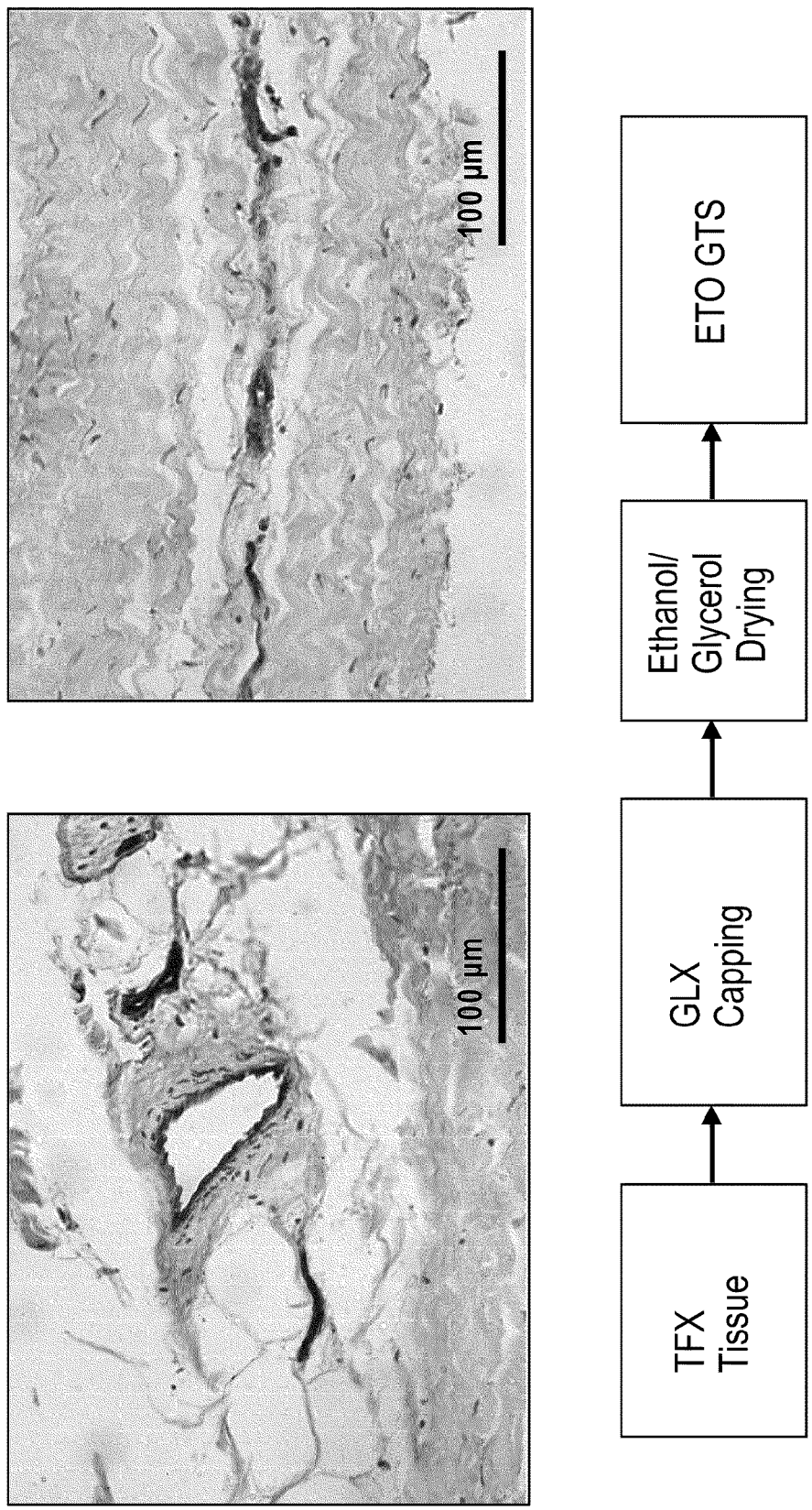
FIG. 7 shows α-Gal and DNA expression as darker areas on fixed tissue treated with a capping, reduction, and drying process.

TFX tissue was subjected to capping and ethanol/glycerol drying followed by ethylene oxide terminal gas sterilization. FIG. 7 shows the results of this treatment, and also shows a flow-diagram of the process used for this experiment, also described above. The presence of staining demonstrates the inability of TFX treatment combined with capping to block the binding of α-Gal antibody to the tissue.

Figure 8:
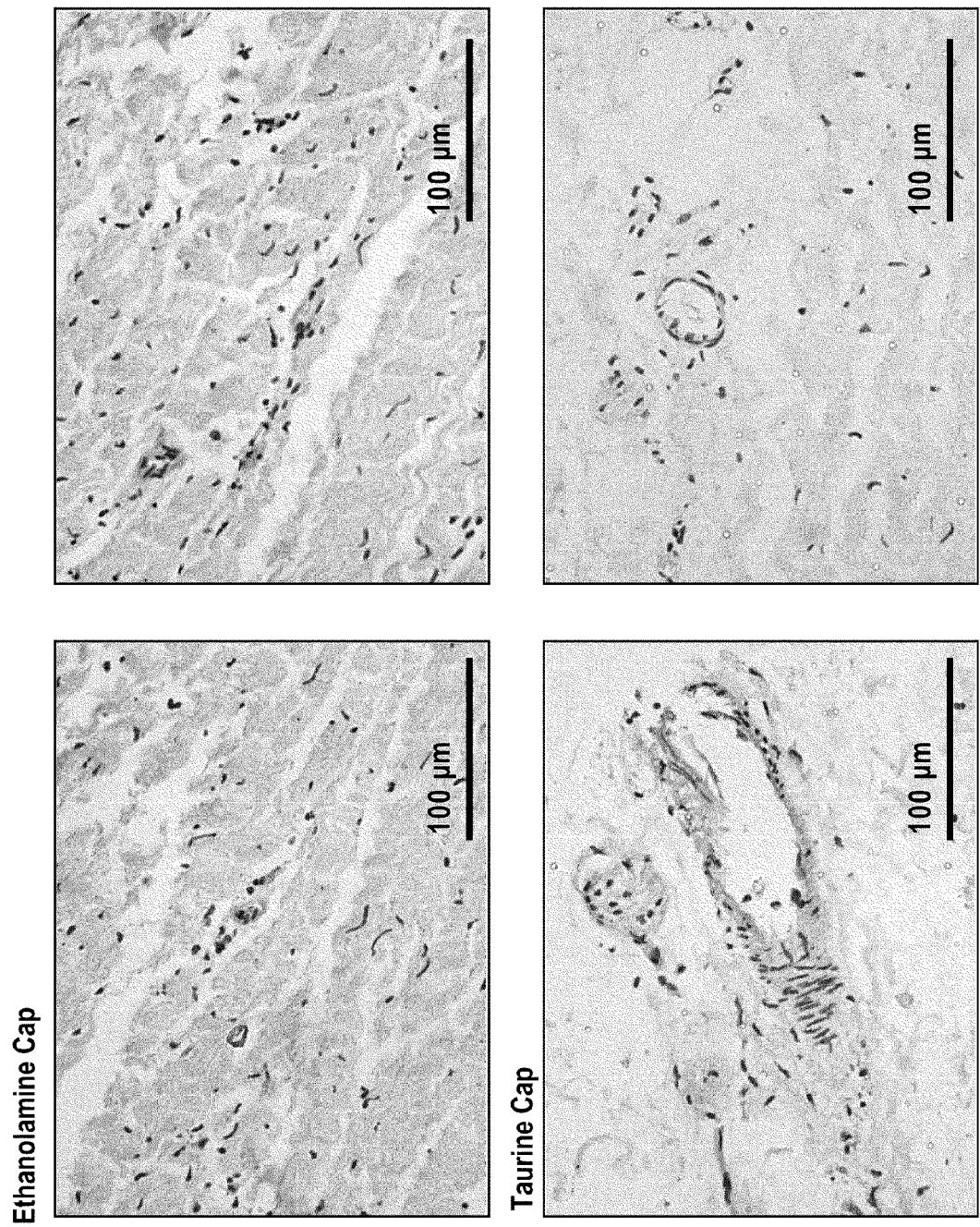
FIG. 8 shows α-Gal and DNA expression as darker areas on fixed tissue treated with the combined treatment e with TFX and vicinal diol (i.e., vic Diol) oxidation, treatment with a capping agent, treatment with a reducing/stabilizing agent, and drying as described herein. The upper panels show tissue treated with ethanolamine. The lower panels show tissue treated with taurine. Brown is α-Gal (Isolectin-IB4, DAB) and Blue is nuclei (Hematoxylin staining).

TFX tissue was subjected to treatment with periodate, a capping agent, a reducing agent, and drying. FIG. 8 shows the results of fixed tissue having received such combined treatment. The upper panels show tissue treated with ethanolamine as the capping agent. The lower panels show tissue treated with taurine as the capping agent. The absence of dark staining demonstrates the inability of α-Gal antibody to bind the fixed tissue following the combined treatment.

Example 5

Comparative Analysis of Tissue Treatments

Relative levels of free α-Gal in variously treated tissues were compared by an ELISA assay. Six tissue samples were treated by distinct combinations of fixation/non-fixation; treatment according to the methods described herein (vic Diol oxidation, treatment with a capping agent and treatment with a stabilizing agent); TFX treatment; capping, reduction and drying; and glutaraldehyde treatment alone. The six tissue treatments compared are as follows: (1) unfixed bovine pericardium; (2) Treatment A: unfixed, bovine pericardium treated with a vic Diol oxidizing agent, a capping agent and a stabilizing agent; (3) Treatment B: TFX-treated bovine pericardium; (4) Treatment C: bovine pericardium treated with a combination of TFX treatment and a vic Diol oxidizing agent, a capping agent and a stabilizing agent; (5) Treatment D: bovine pericardium treated with a capping agent, a reducing agent, and then dried; (6) Treatment E: bovine pericardium treated with a combined treatment of a vic Diol oxidizing agent, a capping agent and a reducing/stabilizing agent and drying; and (7) glutaraldehyde-fixed primate pericardium.

Figure 9:
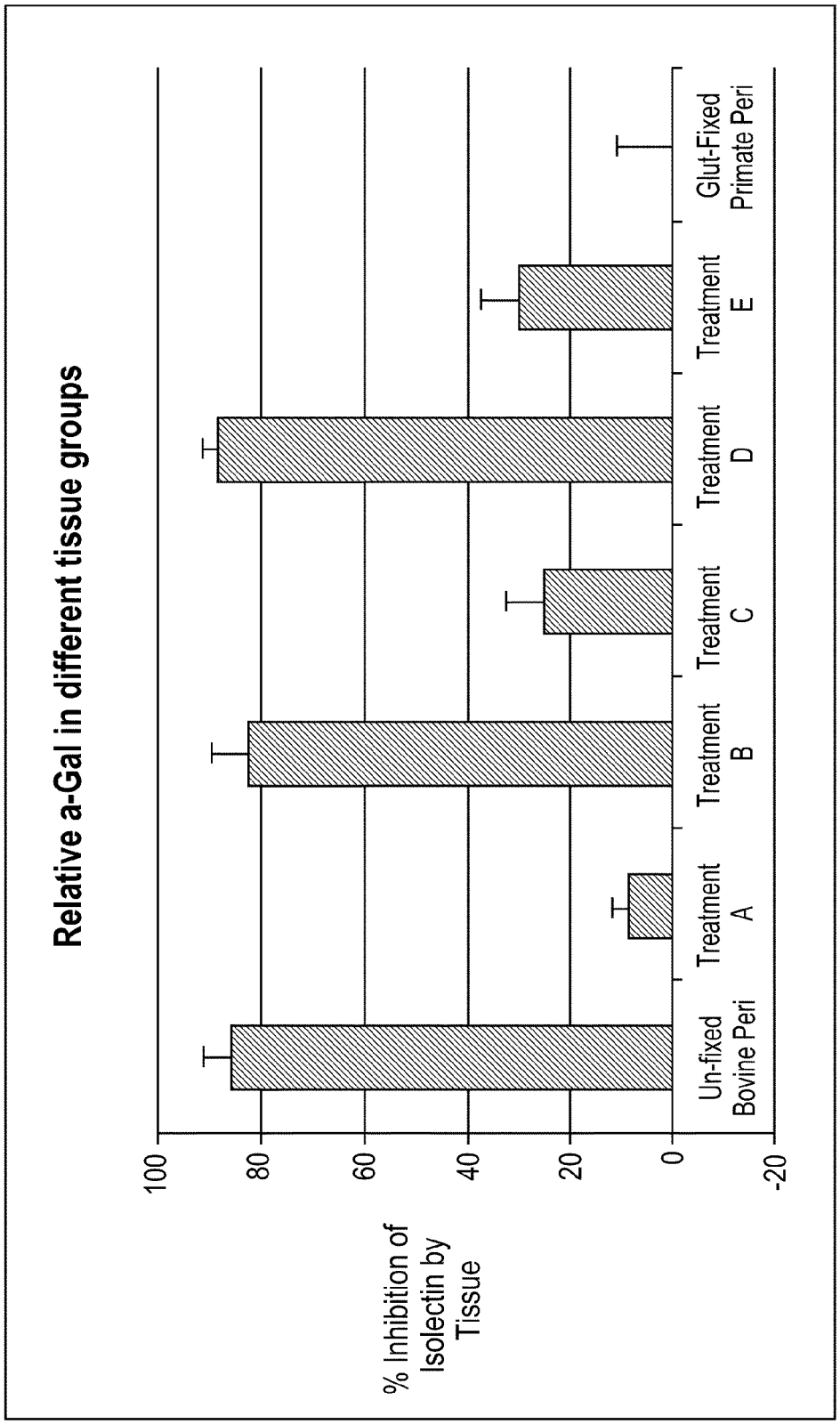
FIG. 9 shows the percent of total isolectin-B4-α-Gal binding inhibition as induced by various tissue treatments and as compared to a control.

Following tissue treatment as specified above and in FIG. 9, each sample was incubated with isolectin-B4, which is known to specifically bind to α-Gal. After overnight incubation, the isolectin-B4 remaining in solution was measured using a standard ELISA assay. Specifically, the tissue samples were cut into small pieces, frozen in liquid nitrogen and ground into a powder. A solution of biotin conjugated, $IB_4$-isolectin (Invitrogen #121414) and 1% BSA (Albumin, bovine serum; Sigma #A7030) were added to the ground tissue and incubated @ 37° C. overnight. The samples were then centrifuged to pellet tissue pieces to the bottom of the tube and the supernatant was transferred to a new tube. Samples were diluted before adding to the plate for $IB_4$-isolectin quantification.

As ELISA assay was performed using Isolectin-B4 in 1% BSA as a standard. Plates were coated with synthetic a-Gal-BSA (V-Labs, Ca$_t$#NGP1334) in carbonate buffer overnight at 4° C. The plate was washed three times with PBS containing Tween (0.01%) and then blocked in 1% BSA for 2 hours at 37° C. A standard curve using Isolectin was added to the plate and the diluted samples from above were added to the plate in triplicate. These were incubated for 1 hr at 37° C. The plate was washed 3 times with PBS-Tween. Vectastain substrate (Vector Labs, cat#PK-6100) was added to the plate and incubated for 30 minutes at room temperature. The plate was washed 3 times with PBS-Tween and once with PBS only. Residual PBS was carefully removed using an aspirator. Quantablu fluorescent substrate (Pierce, Cat#15169) was added and the plate was incubated for 20 minutes. Stop solution was then added and the plate was read on a plate reader (Excitation: 320 nm, Emission: 420 nm).

The concentration of isolectin-B4 remaining in solution was used to calculate the percent of total isolectin that is inhibited by the treated tissue relative to a control. FIG. 9 shows the results of the in vitro α-Gal ELISA assay for the variously treated tissues. As demonstrated in FIG. 9, the tissues treated with the methods described herein exhibited a significant reduction in binding between α-Gal and isolectin-B4. These results indicate that the presently claimed tissue treatment methods significantly reduce the quantity of free α-Gal epitopes and thus reduce the antigenicity of treated tissues.

Example 6

Anti-α-Gal IgG Primate Study

A series of comparative analyses were conducting characterizing the anti-α-Gal IgG response in a group of five primates. Animal implantation was performed at MPI Research. Five macaques were used for this study. Different combinations of test groups were implanted in the animals as described below in order to see the immune response to tissue treatments with or without α-Gal. Six 6 mm tissue discs were implanted intramuscularly in the back of each animal. Three discs were implanted on one side and three discs were implanted on the other side. Blood samples (2 ml per time point) were collected before implant (baseline) and at 5, 10, 20, 45, 60, 75, 90, and 125 days after implant. The study was terminated at 135 days. The blood was stored on dry ice and allowed to clot. Each sample was centrifuged and the serum was transferred to a pre-labeled tube and stored in a −70° C. freezer.

The plate was coated with synthetic α-Gal-BSA (V-Labs, Cat#NGP1334) in carbonate buffer overnight at 4° C. The plate was washed three times with PBS containing Tween (0.01%) and then blocked in 1% BSA for 2 hours at 37° C. The serum from different monkeys and different time points was plated at different dilutions on the plate in duplicate. The serum was incubated for one hour at 37° C. The plate was then washed 3 times in PBS-Tween. The secondary antibody, HRP conjugated, mouse anti-human IgG (Invitrogen, Cat#05-4220; 1:1000 in 1% BSA) was added to the plate and incubated for 1 hour at room temperature. The plate was washed 3 times with PBS-Tween and once with PBS only. The residual PBS was removed by aspirator and o-phenylenediamine dihydrochloride substrate (Sigma, Cat#P8806) was added and incubated for 20 minutes at room temperature. 3M sulfuric acid was added to stop the solution and the absorbance of the plate is read using a plate reader (@492 nm).

The first monkey received three glutaraldehyde-treated tissue samples and three TFX-treated tissue samples. Both sample types produced an anti-α-Gal response in the monkey. Previous experiments have demonstrated high calcification for glutaraldehyde and TFX-treated tissues (data not shown). Monkeys two and three each received three capped/reduced/dried tissue samples and three tissue samples treated according to the method described herein. An anti-α-Gal response was observed. Previous experiments have demonstrated low calcification for both of these types of treated tissue samples (data not shown). The fourth monkey received four samples of tissue treated according to the method described herein and two primate tissue samples. Neither the treated tissue samples nor the control produced an anti-α-Gal response. The fifth monkey received six samples of primate pericardium as a control. The primate pericardium did not produce an anti-α-Gal response.

Figure 10:
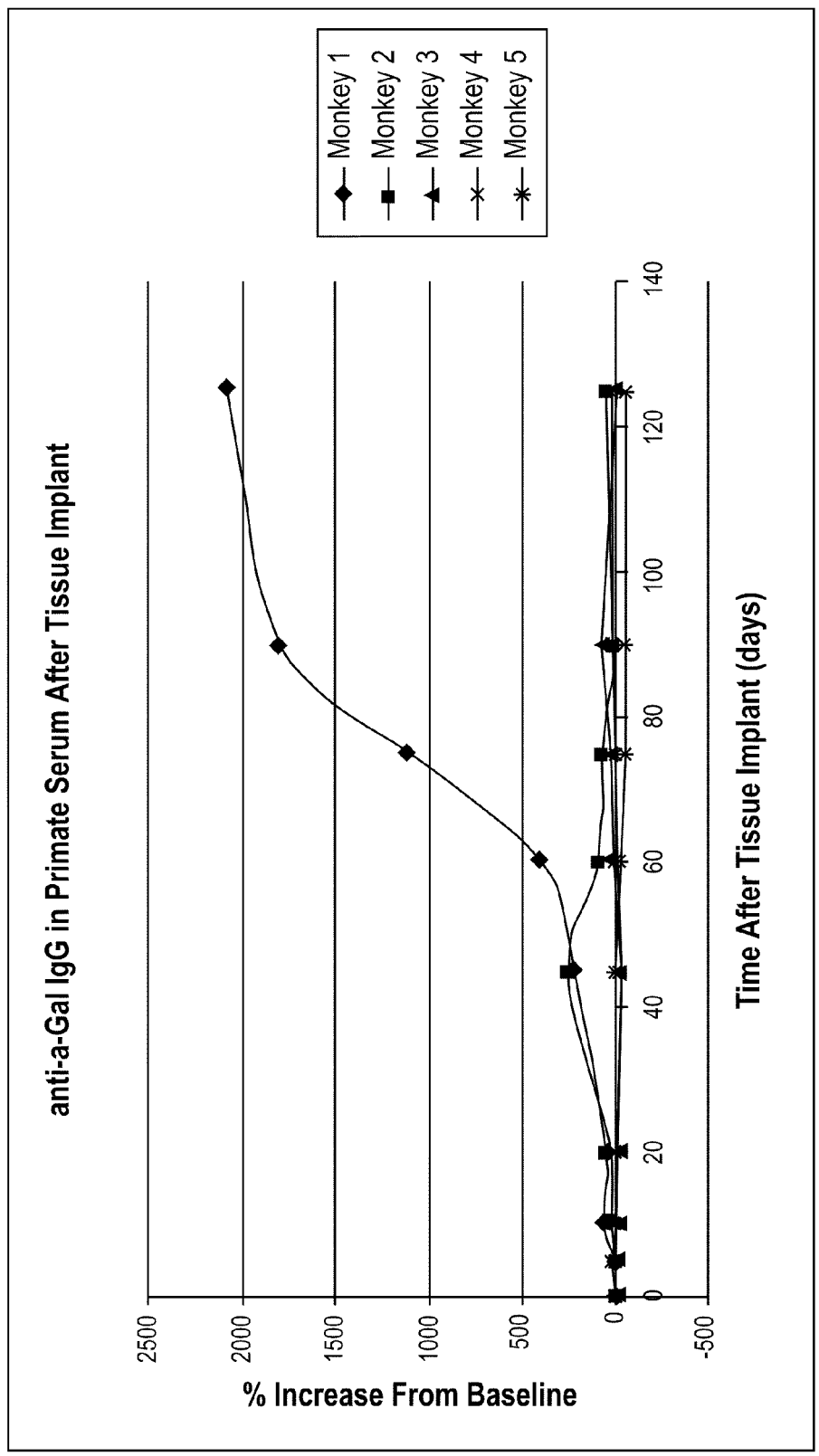
FIG. 10 shows the anti-α-Gal response for the following treatments: glutaraldehyde; TFX; vic Diol oxidation, treatment with a capping agent, and treatment with a stabilizing agent; and a capping, reduction and drying treatment in primate subjects. Data is given as a percent increase or decrease in absorbance compared to an original value.

FIG. 10 shows the percent increase from baseline in the anti-α-Gal IgG response assay for each of the various tissue treatments as described in detail above. As demonstrated in FIG. 10, the presently claimed tissue treatment significantly suppressed the anti-α-Gal response in xenographic tissue samples.

The invention being thus described, it will be obvious that the same can be varied in many ways. Such variations are not to be regarded as a departure from the spirit and scope of the invention, and all such modifications as would be obvious to one skilled in the art are intended to be included within the scope of the following claims.

What is claimed:

1. A method for improving the performance of a bioprosthetic implant, the method comprising:
   treating a fixed bioprosthetic tissue with an oxidizing agent that selectively oxidizes antigenic carbohydrates having vicinal diols to produce free aldehyde or acid moieties on the antigenic carbohydrate and
   treating the bioprosthetic tissue with a capping agent, the capping agent comprising a primary amine or alcohol which combines with the aldehyde or acid to form an imine, amide or ester.

2. The method of claim 1, further comprising treating the bioprosthetic tissue with a stabilizing agent, the agent converting the imine to a secondary amine or the ester to an amide.

3. The method of claim 1, wherein the antigenic carbohydrate is N-glycolylneuraminic acid (Neu5Gc) or the Forssman antigen (GalNAc alpha1,3GalNAc beta1,3Gal alpha1,4Gal beta1,4Glc-Cer).

4. The method of claim 1, wherein the antigenic carbohydrate comprises an α-galactosyl (α-Gal) epitope.

5. The method of claim 1, wherein the oxidizing agent is capable of selectively oxidizing the vicinal diol of the antigenic carbohydrate relative to .beta.-aminoalcohol and vicinal diketone groups comprising the bioprosthetic tissue.

6. The method of claim 1, wherein the oxidizing agent is a periodate or acetate.

7. The method of claim 6, wherein the periodate is sodium periodate.

8. The method of claim 7, wherein the sodium periodate is used at a concentration of 20 mM and wherein the bioprosthetic tissue is treated with the sodium periodate for about 4 hours at about 25° C.

9. The method of claim 1, wherein the capping agent is $R^4$-M-$NH_2$, wherein: $R^4$ is H, $C_{1-6}$ alkyl, $S(=O)_2OR^5$, $C_{1-6}$ alkoxy, or hydroxyl; M is a linker, wherein the linker is $C_{1-6}$ alkylene; and $R^5$ is H or $C_{1-6}$ alkyl.

10. The method of claim 9, wherein the capping agent is an amine, alkyl amine, hydroxylamine, aminoether, amino sulfonate, or a combination thereof.

11. The method of claim 9, wherein $R^4$ is $C_{1-6}$ alkoxy.

12. The method of claim 9 wherein $R^4$ is H.

13. The method of claim 9, wherein $R^4$ is $S(=O)_2OR^5$ and $R^5$ is H.

14. The method of claim 1, wherein the capping agent is ethanolamine, taurine, ethylamine, or 2-methoxyethylamine.

15. The method of claim 2, wherein the stabilizing agent is a reducing agent.

16. The method of claim 15, wherein the reducing agent is selected from the group consisting of sodium borohydride and sodium cyanoborohydride.

17. The method of claim 1, wherein the bioprosthetic tissue is treated with the oxidizing agent in the presence of the capping agent.

18. The method of claim 1, wherein the bioprosthetic tissue is washed to remove the oxidizing agent prior to treatment with the stabilizing agent.

19. The method of claim 1, wherein the bioprosthetic tissue has been treated with one or more of a surfactant and a fixative agent.

20. The method of claim 19, wherein the fixative agent is selected from the group consisting of an aldehyde, a dialdehyde, a diisocyanate, a carbodiimide, a photooxidation agent, and a polyepoxy compound.

21. The method of claim 19, wherein the surfactant is selected from the group consisting of an anionic surfactant, an alkyl sulfonic acid salt, a polyoxyethylene ether, a pluronic or tetronic surfactant, and an alkylated phenoxypolyethoxy alcohol.

22. The method of claim 19, wherein the bioprosthetic tissue has been treated with glutaraldehyde.

23. The method of claim 19, wherein the bioprosthetic tissue has been treated with a surfactant and a fixative agent.

24. The method of claim 1, wherein the bioprosthetic implant is a heart valve.

25. The method of claim 24, wherein the bioprosthetic tissue is bovine pericardium or porcine aortic valve.

26. The method of claim 25, wherein the bioprosthetic implant is a configured for implantation into a pediatric patient.

27. The method of claim 1, wherein the treated bioprosthetic tissue is substantially non-immunogenic in a human host.

28. The method of claim 1, wherein the antigenic carbohydrate of the treated bioprosthetic tissue is substantially non-antigenic in a human host.

29. The method of claim 1, wherein the treated bioprosthetic tissue is substantially non-calcifying in a human host.

30. The method of claim 29, wherein the human host is a pediatric patient.

31. The method of claim 1, further comprising treating the bioprosthetic tissue with one or more of surfactant and a fixative agent.

32. The method of claim 31, wherein the fixative agent is an aldehyde fixative agent.

33. The method of claim 32, wherein the aldehyde fixative agent is glutaraldehyde.

34. The method of claim 31, wherein the fixative agent is a diacid or a diamine with a carbodiimide (EDC).

35. The method of claim 31, wherein the fixative agent is diepoxy.

36. The method of claim 1, wherein the bioprosthetic tissue is a fresh tissue.

37. The method of claim 1, further comprising treating the bioprosthetic tissue with a bioburden reduction solution comprising formaldehyde, ethanol, and a polyethylene sorbital ester solution.

38. The method of claim 1, further comprising drying the bioprosthetic tissue with ethanol and glycerol.

39. The method of claim 1, further comprising sterilizing the bioprosthetic tissue with ethylene oxide.

40. The method of claim 1, further comprising decellularizing the bioprosthetic tissue with a decellularization method comprising treating the tissue with 0.1% SDS, rinsing the tissue, and treating the tissue with DNAse.

41. The method of claim 1, further comprising drying and electrophoretically cleaning the bioprosthetic tissue.

42. The method of claim 1, further comprising sterilizing the bioprosthetic tissue with glutaraldehyde.

43. The method of claim 1, further comprising treating the bioprosthetic tissue with a bioburden reduction solution comprising ethanol and a polyethylene sorbital ester solution.

44. A method for improving the performance of a bioprosthetic implant, the method comprising the steps of:
    obtaining the bioprosthetic tissue, wherein the bioprosthetic tissue is a fresh tissue;
    fixing the bioprosthetic tissue with a fixation agent comprising glutaraldehyde;
    treating the bioprosthetic tissue with a bioburden reduction solution comprising formaldehyde, ethanol, and a polyethylene sorbital ester solution;
    treating the bioprosthetic tissue with an oxidizing agent that selectively oxidizes antigenic carbohydrates having vicinal diols to produce free aldehyde or acid moieties on the antigenic carbohydrate;
    treating the bioprosthetic tissue with a capping agent, wherein the capping agent comprises a primary amine or an alcohol, wherein the primary amine interacts with the aldehyde to form an imine, or an acid to form an amide; and the alcohol interacts with the acid to form an ester;
    treating the bioprosthetic tissue with a stabilizing agent, wherein the stabilizing agent interacts with the imine to form a secondary amine and esters to form an amide;
    drying the bioprosthetic tissue with ethanol and glycerol; and
    sterilizing the bioprosthetic tissue with ethylene oxide.

45. The method of claim 44, wherein the oxidizing agent is a periodate.

46. The method of claim 44, wherein the stabilizing agent is a reducing agent.

47. The method of claim 44, further comprising at least partially fabricating a bioprosthetic product or device from the bioprosthetic tissue using a fabrication device.

48. The method of claim 44, wherein the drying is performed after the fixing and the treating steps.

\* \* \* \* \*